US012721574B2

(12) United States Patent
Burns

(10) Patent No.: US 12,721,574 B2
(45) Date of Patent: Sep. 1, 2026

(54) PRESSURE MEASUREMENT

(71) Applicant: BRUIN BIOMETRICS, LLC, Los Angeles, CA (US)

(72) Inventor: Martin F. Burns, Los Angeles, CA (US)

(73) Assignee: BRUIN BIOMETRICS, LLC, Los Angeles, CA (US)

( * ) Notice: Subject to any disclaimer, the term of this patent is extended or adjusted under 35 U.S.C. 154(b) by 785 days.

(21) Appl. No.: 17/776,752

(22) PCT Filed: Nov. 11, 2020

(86) PCT No.: PCT/US2020/060067
§ 371 (c)(1),
(2) Date: May 13, 2022

(87) PCT Pub. No.: WO2021/096996
PCT Pub. Date: May 20, 2021

(65) Prior Publication Data

US 2022/0395235 A1 Dec. 15, 2022

Related U.S. Application Data

(60) Provisional application No. 63/109,026, filed on Nov. 3, 2020, provisional application No. 62/936,381, filed on Nov. 15, 2019.

(51) Int. Cl.
*A61B 5/00* (2006.01)
*A61B 5/103* (2006.01)
*G16H 50/30* (2018.01)

(52) U.S. Cl.
CPC .......... *A61B 5/7275* (2013.01); *A61B 5/1036* (2013.01); *A61B 5/447* (2013.01); *A61B 5/6892* (2013.01); *G16H 50/30* (2018.01)

(58) Field of Classification Search
CPC ........ A61B 5/7275; A61B 5/447; A61B 5/445
See application file for complete search history.

(56) References Cited

U.S. PATENT DOCUMENTS 5,010,772 A 4/1991 Bourland et al.
6,013,031 A 1/2000 Mendlein et al.
(Continued)

FOREIGN PATENT DOCUMENTS

CA 2620288 A1 8/2009
CN 104219994 A 12/2014
(Continued)

OTHER PUBLICATIONS

Bates-Jensen et al., “Subepidermal Moisture Detection of Pressure Induced Tissue Damage on the Trunk: The Pressure Ulcer Detection (PUD) Study Outcomes”, May 2017, Wound Repair Regen. 25(3): 502-511. doi:10.1111/wrr.12548. (Year: 2017).*
(Continued)

*Primary Examiner* — Mi’schita’ Henson
(74) *Attorney, Agent, or Firm* — Arnold & Porter Kaye Scholer LLP

(57) ABSTRACT

The present disclosure provides methods and apparatus for evaluating tissue structure in damaged or healing tissue. The present disclosure also provides methods of identifying a patient at the onset of risk of pressure ulcer or at risk of the onset of pressure ulcer, and treating the patient with anatomy-specific clinical interventions selected, based on pressure measurements. The present disclosure also provides methods of stratifying groups of patients based on risk of wound development and methods of reducing incidence of tissue damage in a care facility. The present disclosure also provides methods to analyze trends of pressure values
(Continued)

to detect tissue damage before it is visible, and methods to compare bisymmetric pressure values to identify damaged tissue.

17 Claims, 9 Drawing Sheets

(56) References Cited

U.S. PATENT DOCUMENTS

| | | | | |
|---|---|---|---|---|
| 6,287,253 | B1 | 9/2001 | Ortega et al. | |
| 8,971,984 | B2 * | 3/2015 | Freeman | A61B 5/4884 600/475 |
| 9,320,665 | B2 | 4/2016 | Main et al. | |
| 10,020,075 | B2 | 7/2018 | Perlman et al. | |
| 10,028,676 | B2 * | 7/2018 | Freeman | G16Z 99/00 |
| 11,395,622 | B2 * | 7/2022 | Linders | G01K 13/20 |
| 12,133,763 | B2 | 11/2024 | Burns | |
| 12,502,076 | B2 * | 12/2025 | Tran | A61B 5/0022 |
| 2003/0220581 | A1 | 11/2003 | Ollmar et al. | |
| 2005/0165284 | A1 * | 7/2005 | Gefen | A61B 5/103 600/557 |
| 2006/0065060 | A1 | 3/2006 | Ito et al. | |
| 2007/0197904 | A1 | 8/2007 | Viglianti et al. | |
| 2008/0103207 | A1 | 5/2008 | Dayan | |
| 2008/0132808 | A1 | 6/2008 | Lokhorst et al. | |
| 2008/0194928 | A1 | 8/2008 | Bandic et al. | |
| 2008/0279438 | A1 | 11/2008 | West et al. | |
| 2009/0068685 | A1 | 3/2009 | Streeper et al. | |
| 2009/0070939 | A1 | 3/2009 | Hann et al. | |
| 2010/0158332 | A1 | 6/2010 | Rico et al. | |
| 2010/0172567 | A1 | 7/2010 | Prokoski | |
| 2010/0268111 | A1 * | 10/2010 | Drinan | A61B 5/0531 602/43 |
| 2010/0324455 | A1 * | 12/2010 | Rangel | A61B 5/6807 36/43 |
| 2011/0215930 | A1 | 9/2011 | Lee et al. | |
| 2011/0301441 | A1 | 12/2011 | Bandic et al. | |
| 2012/0232403 | A1 | 9/2012 | Smith | |
| 2013/0006151 | A1 | 1/2013 | Main et al. | |
| 2014/0092288 | A1 | 4/2014 | Hattery et al. | |
| 2015/0164467 | A1 | 6/2015 | Suetoshi et al. | |
| 2016/0113667 | A1 | 4/2016 | Bailey et al. | |
| 2016/0135731 | A1 | 5/2016 | Drennan | |
| 2016/0253800 | A1 | 9/2016 | Gurevich et al. | |
| 2017/0196489 | A1 | 7/2017 | Horras et al. | |
| 2017/0224271 | A1 | 8/2017 | Lachenbruch et al. | |
| 2017/0236281 | A1 | 8/2017 | Dacosta | |
| 2017/0311807 | A1 | 11/2017 | Fu et al. | |
| 2017/0325683 | A1 | 11/2017 | Larson et al. | |
| 2017/0347891 | A1 | 12/2017 | Rogers et al. | |
| 2018/0042483 | A1 | 2/2018 | Bardhan et al. | |
| 2018/0098727 | A1 | 4/2018 | Spahn et al. | |
| 2018/0360344 | A1 | 12/2018 | Burns et al. | |
| 2019/0021650 | A1 | 1/2019 | Lee et al. | |
| 2019/0100802 | A1 | 4/2019 | Sanada et al. | |
| 2019/0104982 | A1 | 4/2019 | Dunn et al. | |
| 2019/0125248 | A1 | 5/2019 | Curtin | |
| 2019/0142333 | A1 | 5/2019 | Burns et al. | |
| 2019/0160116 | A1 | 5/2019 | Muller et al. | |
| 2019/0175098 | A1 | 6/2019 | Burns et al. | |
| 2019/0246972 | A1 | 8/2019 | Burns et al. | |
| 2019/0307904 | A1 | 10/2019 | Ballamy | |
| 2020/0009123 | A1 | 1/2020 | Hakozaki et al. | |
| 2020/0104997 | A1 | 4/2020 | Takagi | |
| 2022/0386941 | A1 | 12/2022 | Burns | |
| 2022/0400956 | A1 | 12/2022 | Burns | |
| 2022/0401015 | A1 | 12/2022 | Burns | |
| 2022/0401063 | A1 | 12/2022 | Burns | |
| 2025/0017555 | A1 | 1/2025 | Burns | |

FOREIGN PATENT DOCUMENTS

| | | | | |
|---|---|---|---|---|
| JP | 2004-105446 | A | 4/2004 | |
| JP | 2013-510620 | A | 3/2013 | |
| JP | 2016-224396 | A | 12/2016 | |
| JP | 2017-012427 | A | 1/2017 | |
| JP | 2018-089368 | A | 6/2018 | |
| JP | 2018-093901 | A | 6/2018 | |
| WO | 2011/058457 | A1 | 5/2011 | |
| WO | 2013/114356 | A1 | 8/2013 | |
| WO | 2013/151705 | A9 | 10/2013 | |
| WO | WO-2017048979 | A1 * | 3/2017 | A61B 5/447 |
| WO | 2019/099810 | A1 | 5/2019 | |
| WO | 2019/178583 | A1 | 9/2019 | |
| WO | 2021/096992 | A1 | 5/2021 | |
| WO | 2021/096994 | A9 | 5/2021 | |
| WO | 2021/097033 | A1 | 5/2021 | |
| WO | 2021/097037 | A2 | 5/2021 | |
| WO | 2021/097079 | A1 | 5/2021 | |
| WO | 2021/097081 | A1 | 5/2021 | |
| WO | 2021/097083 | A1 | 5/2021 | |
| WO | WO-2021096994 | A1 * | 5/2021 | A61B 5/447 |
| WO | 2021/096993 | A1 | 6/2021 | |

OTHER PUBLICATIONS

Gehen, "The future of pressure ulcer prevention is here: Detecting and targeting inflammation early", 2018, EWMA Journal, vol. 19 No. 2, pp. 7-13 (Year: 2018).*

Kanno et al., "Low-Echoic Lesions Underneath the Skin in Subjects with Spinal-Cord Injury," *Spinal Cord*, 47:225-229 (2009).

Scheiner et al., "Ultrasound to Detect Pressure-Related Deep Tissue Injuries in Adults Admitted via the Emergency Department: A Prospective, Descriptive, Pilot Study," *Ostomy Wound Management*, 63(3):36-46 (2017).

Supplementary European Search Report for European Application 20886304, completed May 30, 2023.

Supplementary European Search Report for European Application 20888629, completed May 30, 2023.

Supplementary European Search Report for European Application 20887519, completed Oct. 11, 2023.

Yabunaka et al., "Three-Dimensional Ultrasound Imaging of the Pressure Ulcer. A Case Report," *Med. Ultrason.*, 17(3):404-406 (2015).

Aoi et al., "Ultrasound Assessment of Deep Tissue Injury in Pressure Ulcers: Possible Prediction of Pressure Ulcer Progression," *Plastic and Reconstructive Surgery*, 124(2):542-549 (2009).

Bergstrom et al., "The Braden Scale for Predicting Pressure Sore Risk," *Nurs. Res.*, 36(4):205-210 (1987), Lippincott Williams & Wilkins (publisher), Philadelphia, PA.

Brem et al., "High Cost of Stage IV Pressure Ulcers," *Am. J. Surg.*, 200(4):473-477 (2010), Elsevier (publisher), Amsterdam, Netherlands.

Garcia-Fernandez, "Predictive Capacity of Risk Assessment Scales and Clinical Judgment for Pressure Ulcers: A Meta-Analysis," *Journal of Wound Ostomy & Continence Nursing*, 41:24-34 (2014), Lippincott Williams & Wilkins (publisher), Philadelphia, PA.

Huong et al., "Multispectral Imaging of Acute Wound Tissue Oxygenation," *J. Innov. Opt. Health Sci.*, 10(3):1750004, 8 pp. (2017), World Scientific Publishing Co. Pte Ltd. (publisher), Singapore.

International Search Report for PCT/US2020/060067 dated Mar. 17, 2021.

International Search Report for PCT/US2020/060211 dated Mar. 17, 2021.

International Search Report for PCT/US2020/060062 dated Mar. 18, 2021.

International Search Report for PCT/US2020/060063 dated Mar. 18, 2021.

International Search Report for PCT/US2020/060219 dated Mar. 18, 2021.

International Search Report for PCT/US2020/060064 dated Mar. 25, 2021.

International Search Report for PCT/US2020/060145 dated Mar. 25, 2021.

International Search Report for PCT/US2020/060222 dated Mar. 25, 2021.

(56) References Cited

OTHER PUBLICATIONS

International Search Report for PCT/US2020/060151 dated May 7, 2021.

The National Institute for Health and Care Excellence (NICE), "Pressure Ulcers: Prevention and Management," Clinical Guideline, 29 pp. (Apr. 23, 2014), National Institute for Health and Care Excellence (publisher), London, England.

Nelissen et al., "An Advanced Magnetic Resonance Imaging Perspective on the Etiology of Deep Tissue Injury," *J. Appl. Physiol.*, 124(6):1580-1596 (2018), American Physiological Society (publisher), Rockville, Maryland.

Pancorbo-Hidalgo et al., "Risk Assessment Scales for Pressure Ulcer Prevention: A Systematic Review," *Journal of Advanced Nursing*, 54:94-110 (2006), Wiley (publisher), Hoboken, New Jersey.

Ruan et al., "Magnetic Resonance Imaging of Nonhealing Pressure Ulcers and Myocutaneous Flaps," *Archives of Physical Medicine and Rehabilitation*, 79(9):1080-1088 (1998), Elsevier (publisher), Amsterdam, Netherlands.

Yafi et al., "Quantitative Skin Assessment Using Spatial Frequency Domain Imaging (SFDI) in Patients with or at High Risk for Pressure Ulcers," *Lasers in Surgery and Medicine*, 49(9):827-834 (2017), Wiley-Liss Inc. (publisher), New York, NY.

Yudovsky et al., "Assessing Diabetic Foot Ulcer Development Risk with Hyperspectral Tissue Oximetry," *J. Biomed. Optics*, 16(2):026009, 8 pp. (2011), SPIE (publisher), Bellingham, WA.

Anonymous, "Wound Home Skills Kit: Pressure Ulcers," American College of Surgeons, Division of Education, Surgical Patient Education Program: Prepare for the Best Recovery, https://www.facs.org/media/32hdibi4/wound_pressure_ulcers.pdf (2018).

* cited by examiner

PRESSURE MEASUREMENT

CROSS-REFERENCE TO RELATED APPLICATIONS

This application is a U.S. National Stage under 35 U.S.C. § 371 of International Application No. PCT/US2020/060067 filed Nov. 11, 2020 (published as WO 2021/096996 on May 20, 2021), which claims the benefit of priority of U.S. Provisional Application 62/936,381 filed Nov. 15, 2019, and U.S. Provisional Application 63/109,026 filed Nov. 3, 2020, each of which is herein incorporated by reference in its entirety.

FIELD

The present disclosure provides methods and apparatus for evaluating tissue structure in damaged or healing tissue. The present disclosure also provides methods of identifying a patient at the onset of risk of pressure ulcer or at risk of the onset of pressure ulcer, and treating the patient with anatomy-specific clinical intervention selected based on pressure measurements. The present disclosure also provides methods of stratifying groups of patients based on the risk of wound development, and methods of reducing the incidence or severity of tissue damage in patients admitted to a care facility. The present disclosure also provides methods of detecting tissue damage before the tissue damage is visible on a patient's skin.

BACKGROUND

The skin is the largest organ in the human body. It is readily exposed to different kinds of damages and injuries. Skin damage and injury may result when the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer. In the presence of other damage, such as the neuropathy and peripheral tissue weakening that can be induced by diabetes, even periodic exposure to moderate levels of pressure and stress may lead to an ulcer, for example a foot ulcer.

Pressure ulcers are developed by approximately 2.5 million people a year in the United States and an equivalent number in the European Union. In long-term and critical-care settings, up to 25% of elderly and immobile patients develop pressure ulcers. Approximately 60,000 U.S. patients die per year due to infection and other complications from pressure ulcers.

Most pressure ulcers occur over bony prominences, where there is less tissue for compression and the pressure gradient within the vascular network is altered. Pressure ulcers are categorized in one of six stages, ranging from the earliest stage currently recognized, in which the skin remains intact but may appear red over a bony prominence (Stage 1), to a stage where tissue is broken and bone, tendon or muscle is exposed (Stage 4), to a deep tissue pressure injury stage showing non-blanchable deep red, maroon, or purple discoloration, and finally to a stage where there is obscured full-thickness skin and tissue loss (unstageable).

Detecting pressure ulcers before the skin breaks and treating them to avoid progression to later stages is a goal of policy makers and care providers in major economies. Most pressure ulcers are preventable, and if identified before the first stage of ulceration, deterioration of the underlying tissue can be halted.

Detecting tissue damage before the skin breaks and intervening with the appropriate therapy to avoid further deterioration of the underlying tissue is desirable not only for the patient but society. The average cost of treating pressure-induced damage at the earliest visible sign (a Stage 1 ulcer) is only $2,000 but this rises to $129,000 when the ulcer is deep enough to expose muscle or bone (a Stage 4 ulcer). See, e.g., Brem, H. et al. (2010). High Cost of Stage IV Pressure Ulcers. *Am. J. Surg*. October; 200(4):473-477. Currently, patients normally receive universal prevention of pressure ulcers, meaning that the prevention does not target to any particular anatomical sites. Patients only receive a targeted, localized, treatment of ulcer after the pressure ulcer is developed to the point that it can be identified by a visual assessment. The current standard to detect pressure ulcers is by visual inspection, which is subjective, unreliable, untimely, and lacks specificity. See, e.g., Pancorbo-Hidalgo P. et al. (2006). Risk assessment scales for pressure ulcer prevention: a systematic review. *Journal of Advanced Nursing,* 54, 94-110; Garcia-Fernandez, F. P. (2014). Predictive Capacity of Risk Assessment Scales and Clinical Judgment for Pressure Ulcers: A Meta-analysis. *Journal of wound, Ostomy and Continence Nursing* 41, 24-34. Therefore, even when a patient is experiencing inflammation of the skin, a precursor of ulcer development, he or she would not be receiving a targeted, localized treatment for the developing ulcer. Instead, the inflammation would continue to develop into a full-blown ulcer.

Skin damage and injury may also result from certain types of surgical procedures, for example reconstructive surgery involving skin flaps, which sever blood vessels in or around the area of surgery. Healing of damaged or separated tissue is dependent upon re-establishment of adequate blood flow throughout the damaged area. Determining whether an area of tissue is healing, i.e. that blood flow through the tissue is increasing to a normal level, is difficult to do via visual inspection. Existing equipment can measure certain attributes, such as the oxygenation level of the blood, that are at best indirect measures of blood flow.

Pressure measurements allows the detection of contact pressure on a patient's skin. Pressure measurements may be between the patient and a resting surface. Pressure measurements is inexpensive and non-invasive.

SUMMARY

Systematic methods using non-invasive, objective measurements to identify the onset of the risk of pressure ulcer before visible skin damages, followed by administering individualized intervention at specific anatomy are provided. Systematic methods using non invasive, objective measurements to identify the onset of a pressure ulcer before visible skin damages, followed by administering individualized intervention at specific anatomy are also provided. Methods for monitoring progression of wound healing and consistency of intervention compliance are further provided.

In an aspect, the present disclosure provides for, and includes, a method of assessing pressure measurements on a patient's intact skin, the method comprising the steps of: obtaining pressure measurements at a plurality of locations on the patient's skin, and generating a pressure measurement map.

In an aspect, the present disclosure provides for, and includes, a method of reducing the incidence of tissue damage in patients admitted to a care facility, the method comprising the steps of: evaluating a patient for a risk of tissue damage upon admission to the care facility, administering an intervention of level-0 if the average pressure value is below a first threshold, and administering an intervention of level-N if the average pressure value is above a first threshold, wherein N is an integer and N has a value of 1 or greater. In an aspect, evaluating comprises: taking a pressure measurement of the patient at one or more body locations at risk of wound development, and determining an average pressure value of the pressure measurements.

In an aspect, the one or more body locations at risk of wound development are selected from the group consisting of a sternum, a *sacrum*, a heel, a *scapula* (os *latum scapularum*), an elbow, an ear, and other fleshy tissues over a bony prominence of a patient. In an aspect, the one or more body locations at risk of wound development comprise one or more anatomical sites in long-term contact with a medical device. In an aspect, the body location at risk of wound development is selected from the group consisting of a cheek, a nose, a chest, a stomach, and a lower abdomen area.

In an aspect, the present disclosure provides for, and includes, a method of stratifying a plurality of patients in a care facility based on care levels, the method comprising the steps of: taking a pressure measurement of a patient in the plurality of patients at one or more body locations selected for monitoring, determining an average pressure value of the pressure measurement of the patient, determining a care level of N care levels that corresponds to the average pressure value, assigning the care level to the patient, and arranging the patient of the plurality of patients into groups based on each of the patient's assigned care levels.

In an aspect, the one or more body locations at risk of wound development are selected from the group consisting of a sternum, a *sacrum*, a heel, a *scapula* (os *latum scapularum*), an elbow, an ear, and other fleshy tissues over a bony prominence of a patient. In an aspect, one or more body locations at risk of wound development comprise one or more anatomical sites in long-term contact with a medical device, and are selected from the group consisting of a cheek, a nose, a chest, a stomach, and a lower abdomen area.

In an aspect, the present disclosure provides for, and includes, a method for identifying and providing an appropriate level of care to a patient in a care facility, the method comprising the steps of: taking a plurality of pressure measurements of the patient at one or more body locations, determining an average pressure value of the plurality of pressure measurements of the patient, providing one or more anatomy-specific interventions based on the average pressure value, increasing the level of anatomy-specific interventions based on an increase in the average pressure value, and decreasing the level of anatomy-specific interventions based on a decrease in the average pressure value.

In an aspect, the present disclosure provides for, and includes, a method of assigning a patient in a care facility to a risk category selected from a plurality of risk categories, the method comprising the steps of: taking an initial pressure measurement at one or more locations of the body selected for monitoring, determining an average pressure value of the pressure measurement, and assigning the patient to a risk category selected from the plurality of risk categories, wherein the assigning is based partially on the average pressure value of the pressure measurement.

In an aspect, the locations of the body are selected from the group consisting of a sternum, a *sacrum*, a heel, a *scapula* (os *latum scapularum*), an elbow, an ear, and other fleshy tissues over a bony prominence of a patient. In an aspect, the locations of the body comprise one or more anatomical sites in long-term contact with a medical device, and are selected from the group consisting of a cheek, a nose, a chest, a stomach, and a lower abdomen area.

In an aspect, the present disclosure provides for, and includes, a method of managing care of a patient, the method comprising the steps of: taking a first set of pressure measurements at one or more body locations selected for monitoring upon admission to a care facility, determining a first average pressure value of each of the first set of pressure measurements, setting an intervention level to N=1 if one of the average pressure value of the first set of pressure measurements is above a first threshold, implementing a level-N intervention for each of the one or more body locations having an average pressure value above a first threshold, taking subsequent sets of pressure measurements at each of the one or more body locations at a level-N frequency, and determining new average pressure values for each of the one or more body locations.

In an aspect, the one or more body locations selected for monitoring are selected from the group consisting of a sternum, a *sacrum*, a heel, a *scapula* (os *latum scapularum*), an elbow, an ear, and other fleshy tissues over a bony prominence of a patient. In an aspect, the one or more body locations selected for monitoring comprise one or more anatomical sites in long-term contact with a medical device, and are selected from the group consisting of a cheek, a nose, a chest, a stomach, and a lower abdomen area.

In an aspect, the present disclosure provides for, and includes, a method of identifying and treating a patient at risk of tissue damage, the method comprising the steps of: evaluating a patient for a risk of tissue damage upon admission to a care facility, administering a first intervention of level-0 if the first average pressure value is below or equal to a first threshold; and administering a first intervention of level-N if the first average pressure value is above the first threshold, where N is an integer and N has a value of 1 or greater. In an aspect, the evaluating step comprises: taking a first plurality of pressure measurements in the patient, and determining a first average pressure value of the initial set of pressure measurements.

In an aspect, the method further comprises the steps of: taking a second plurality of pressure measurements in the patient at a first pre-determined frequency corresponding to the administered intervention level, determining a second average pressure value of the second plurality of pressure measurements, determining whether the second average pressure value exceeds a second threshold, continuing to administer the first intervention if the second average pressure value does not exceed the second threshold, continuing to take a plurality of pressure measurements at the first pre-determined frequency if the second average pressure value does not exceed the second threshold, administering a second intervention of level-M if the second average pressure value exceeds the second threshold, where M is an integer and M is greater than N, and taking a plurality of pressure measurements at a second pre-determined frequency corresponding to level-M if the second average pressure value exceeds the second threshold.

In an aspect, the method further comprises the steps of: determining whether the second average pressure value is less than a third threshold, continuing to administer the first intervention if the second average pressure value is not less than the third threshold, continuing to take a plurality of pressure measurements at the first pre-determined frequency if the second average pressure value is not less than the third threshold, administering a third intervention of level-L if the second average pressure value is less than the third threshold and if the first intervention is not of level-0, where L is an integer and L is less than N, and taking a plurality of pressure measurements at a pre-determined frequency corresponding to level-L if the second average pressure value is less than the third threshold.

In an aspect, the first intervention of level-N is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the second intervention of level-M is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the third intervention of level-L is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the first average pressure value is determined from a subset of the first plurality of pressure measurements. In an aspect, the second average pressure value is determined from a subset of the second plurality of pressure measurements.

In an aspect, the second threshold is equal to the first threshold. In an aspect, the third threshold is equal to the first threshold.

In an aspect, the present disclosure provides for, and includes, a method of identifying and treating a patient in need of an intervention for pressure ulcer, the method comprising the steps of: taking a plurality of pressure measurements at an anatomic site of the patient, determining an average pressure value of the plurality of pressure measurements, determining whether the average pressure value exceeds a threshold corresponding to level N, where N is greater than or equal to 2, administering the intervention for pressure ulcer to the anatomic site if the average pressure value exceeds the threshold, and taking a plurality of pressure measurements every two hours if the average pressure value exceeds the threshold.

In an aspect, the anatomical site is selected from the group consisting of a sternum, a *sacrum*, a heel, a *scapula* (os *latum scapularum*), an elbow, an ear, and other fleshy tissues over a bony prominence of a patient. In an aspect, the intervention for pressure ulcer is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the present disclosure provides for, and includes, a method for identifying damaged tissue, the method comprising the steps of: obtaining a first pressure measurement from a first location on a patient's skin, obtaining a second pressure measurement from a second location that is bisymmetric relative to the first location, determining an average pressure value of each of the first and second pressure measurements, determining the average pressure value from each of the first and second pressure measurements, determining a difference in the average pressure value between a first pressure measurement and a second pressure measurement, and determining that there is tissue damage at the first or second location if the difference in average pressure value exceeds a threshold value.

In an aspect, the first location is selected from the group consisting of a sternum, a *sacrum*, a heel, a *scapula* (os *latum scapularum*), an elbow, an ear, and other fleshy tissues over a bony prominence of a patient.

In an aspect, the present disclosure provides for, and includes, a method of detecting tissue damage before it is visible on a patient's skin, the method comprising the steps of: taking a plurality of pressure measurements at a location on the patient's skin at incremental times, determining an average pressure value from each of the plurality of pressure measurements, calculating a slope between the latest average pressure value and the immediately prior average pressure value, comparing the slope to a threshold value, and determining that there is tissue damage if the slope exceeds the threshold value.

In an aspect, the location is selected from the group consisting of a sternum, a *sacrum*, a heel, a *scapula* (os *latum scapularum*), an elbow, an ear, and other fleshy tissues over a bony prominence of a patient. In an aspect, the method is performed at a plurality of locations.

In an aspect, the present disclosure provides for, and includes, a method of detecting tissue damage before it is visible on a patient's skin, the method comprising the steps of: taking a plurality of pressure measurements on the patient's skin at a plurality of locations at incremental times, determining an average pressure value from the each of the plurality of pressure measurements, calculating a pressure difference of the maximum average pressure value and the minimum average pressure value for each time, calculating a derivative of the pressure difference with respect to time, comparing this derivative to a threshold value, and determining that there is tissue damage if the derivative exceeds the threshold value.

In an aspect, the plurality of locations is selected from the group consisting of a sternum, a *sacrum*, a heel, a *scapula* (os *latum scapularum*), an elbow, an ear, and other fleshy tissues over a bony prominence of a patient. In an aspect, the method is performed at a plurality of locations.

In an aspect, the derivative of difference value with respect to time is calculated from the two most recent difference values.

In an aspect, the present disclosure provides for, and includes, a method of detecting tissue damage before it is visible on a patient's skin, the method comprising the steps of: taking a plurality of pressure measurements at a location on the patient's skin at each of a plurality of incremental times, determining an average pressure value from each of the plurality of pressure measurements, calculating a pressure difference of the maximum average pressure value and the minimum average pressure value for each incremental time, fitting a curve to a predetermined number of the most-recent pressure differences, calculating a curvature of the fitted curve, comparing this curvature to a threshold value, and determining that there is tissue damage if the curvature exceeds the threshold value.

In an aspect, the location is selected from the group consisting of a sternum, a *sacrum*, a heel, a *scapula* (os *latum scapularum*), an elbow, an ear, and other fleshy tissues over a bony prominence of a patient. In an aspect, the method is performed at a plurality of locations.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figure 1A:
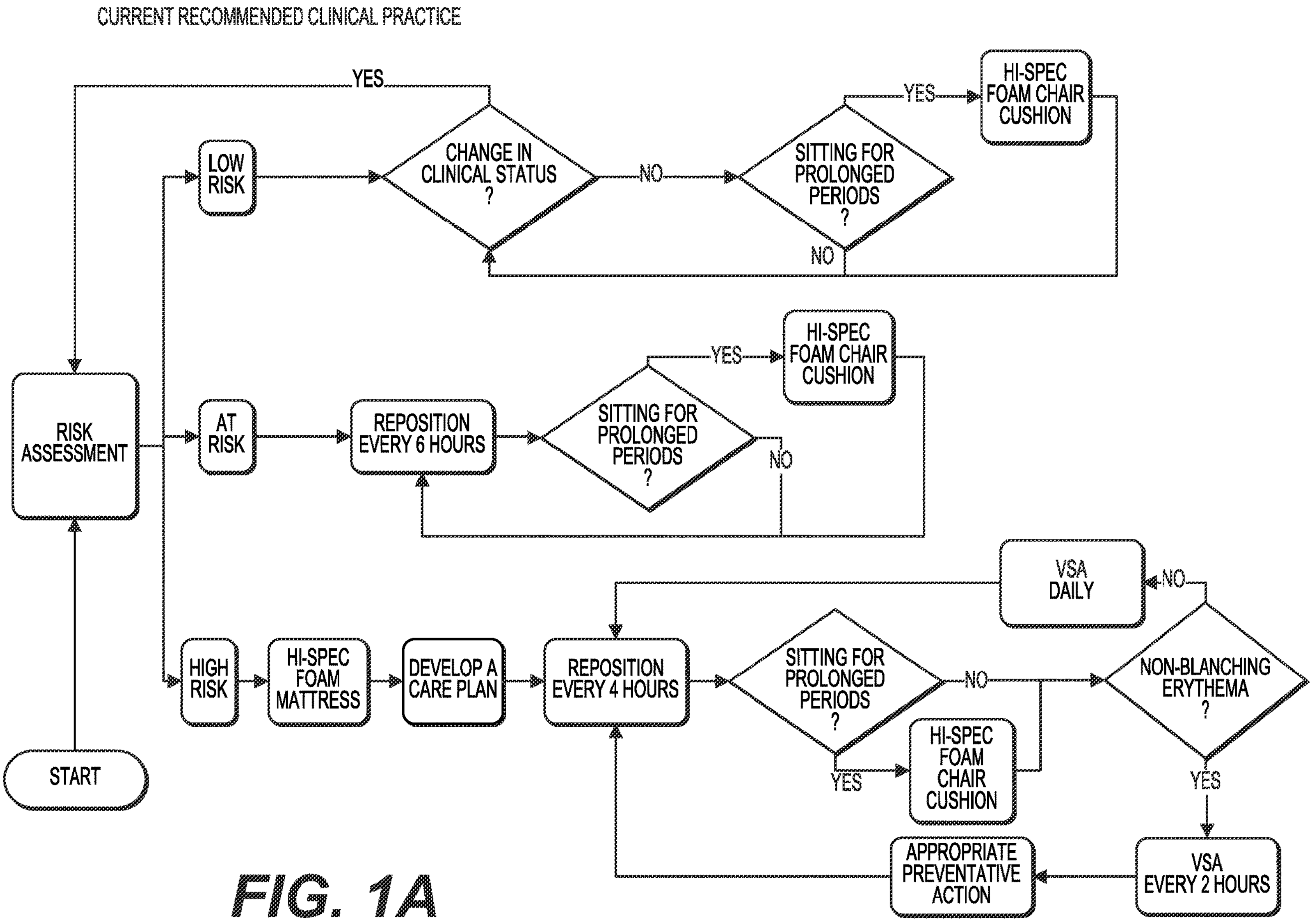
FIG. 1A is an example of a currently recommended treatment decision pathway for preventing pressure ulcers in hospital patients using a combination of risk assessment and visual assessment.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, and which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only, and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a measurement value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "exemplary" is used to mean serving as an example, instance, or illustration. Any embodiment or aspect described as "exemplary" is not necessarily to be construed as preferred or advantageous over other embodiments or aspects, nor is it meant to preclude equivalent structures and techniques known to those of ordinary skill in the art. Rather, use of the word exemplary is intended to present concepts in a concrete fashion, and the disclosed subject matter is not limited by such examples.

As used herein, the term "patient" comprises both human and animal subjects.

As used herein, the term "skin" indicates the surface of a patient's body.

As used herein, the term "tissue" refers to an ensemble of similar cells and their extracellular matrix from the same origin that together carry out a specific function. In some aspects, tissue includes a plurality of layers of the patient's body starting from the stratum corneum and including additional deeper structures such as the epidermis, the dermis, and a portion of deeper tissue that includes blood vessels. In an aspect, tissue does not include the stratum corneum.

As used herein, the term "wound" refers to damaged or injured tissue, which may or may not be visible on the surface of the skin. A wound may be open or closed. A wound may arise from a surgical procedure. A wound may be a burn wound. In an aspect, a wound is a pressure ulcer. In a further aspect, the pressure ulcer is subcutaneous. In one aspect, a pressure ulcer is a pressure ulcer resulting from an extended period of use of a medical device such as, for example, a mask, a tubing, or a strap. In an aspect, a wound is a diabetic foot ulcer. In an aspect, a wound is a vascular ulcer.

As used herein, "tissue biocapacitance" refers to a biophysical marker for detecting initial tissue damage based on the increased level of fluids that build up in the interstitial space. Without being bound by theory, the greater the fluid content in a tissue, the higher the biocapacitance value becomes. In some aspects, the methods described herein comprise a step of measuring the biocapacitance in a tissue. In some aspects, the methods described herein comprise a step of measuring the biocapacitance of the skin.

As used herein, the term "time delta" refers to a calculated difference between two values derived from measurements obtained at different times from a subject. In an aspect, each of the two values is an average value calculated from measurements obtained at approximately the same time. In an aspect, each of the two values is a summation value calculated from measurements obtained at approximately the same time. In an aspect, two measurements are obtained at approximately the same time when they are taken no more than about 10 hours apart, no more than about 8 hours apart, no more than about 6 hours, no more than about 5 hours apart, no more than about 4 hours apart, no more than about 3 hours apart, no more than about 2 hours apart, or no more than about 1 hour apart.

As used herein, the variables "K," "L," "M," and "N" are non-negative integers.

As used herein, the term "anatomy-specific" refers to the application of clinical interventions to the same locations where certain pressure measurements are taken.

As used herein, a "system" may be a collection of devices in wired or wireless communication with each other.

As used herein, "bisymmetric" refers to a pair of locations that are approximately equidistant from a line of symmetry.

As used herein, the term "pressure measuring device" comprises any device that captures pressure information at one or more points distributed across a two-dimensional area. In an aspect, the pressure measuring device is a strain gauge. In an aspect, the pressure measuring device is a piezoresistive strain gauge. In an aspect, the pressure measuring device is a capacitive pressure sensor. In an aspect, the pressure measuring device is a piezoelectric pressure sensor. In an aspect, the pressure measuring device provides information about whether pressure is being applied on a surface. In an aspect, the pressure measuring device measures the absolute pressure applied on a surface.

As used herein, the term "light" means electromagnetic energy having a wavelength within the range of 1 picometer to 1 meter. In an aspect, this range is 1 nanometer to 1 millimeter, encompassing "ultraviolet," "visible," and "infrared" light. In an aspect, this range is 10-390 nanometers, which is commonly understood to be "ultraviolet" light. In an aspect, this range is 390-700 nanometers, which is commonly understood to be "visible" light. In an aspect, this range is 700 nanometers to 1 millimeter, which is commonly understood to be "infrared" radiation. In an aspect, this range is 700-900 nanometers, which is commonly understood to be "near infrared" radiation. In an aspect, this light may be a narrow band of wavelengths about a particular wavelength. In an aspect, the particular wavelength is 760 and/or 830 nanometers.

Within this document, identification of light as having a certain wavelength has the same meaning as identifying the light as having a certain frequency, as the wavelength and frequency of light are uniquely related. Reference to a frequency of light is considered equivalent and interchangeable with a reference to the wavelength of the same light.

As used herein, the term "method" comprises a sequence of activities, e.g. steps. In certain embodiments, the steps must be performed in a particular order while, in other embodiments, the sequence of activities may be interchanged. A "method" is considered equivalent to and interchangeable with a "process." In certain embodiments, one or more disclosed steps are omitted.

Methods of Assessing Pressure Measurements

In an aspect, the present disclosure provides a method of assessing pressure measurements on a patient's intact skin, the method comprising the steps of: obtaining a pressure measurement scan on the patient's skin, and generating a pressure measurement map.

In an aspect, a pressure measurement scan includes obtaining a pressure measurement at a single location on the patient's skin. In an aspect, a pressure measurement scan includes obtaining a pressure measurement at multiple locations on the patient's skin. In an aspect, a pressure measurement scan includes obtaining a plurality of pressure measurements at multiple locations on the patient's skin. In an aspect, evaluating a patient comprises determining an average pressure value of a pressure measurement. In an aspect, evaluating a patient comprises determining an average pressure value of a plurality of pressure measurements. In an aspect, a pressure measurement map shows the map of pressures experienced on the skin.

In an aspect, an average pressure value at a location is obtained from two, three, four, five, six, seven, eight, nine, ten, or more than ten pressure values measured at that location. In one aspect, a pressure difference is determined by the difference between average pressure values derived from measurements taken at two bisymmetric locations with respect to a centerline.

In an aspect, a pressure value may be calculated from a plurality of pressure measurements made at a certain location, or in close proximity around a specific location, in a plurality of methods disclosed herein. In an aspect, a plurality of pressure measurements are made in a pre-determined pattern on the skin and the pressure value is calculated by subtracting the pressure value associated with a pre-determined position within the pattern from the largest pressure value made at the other positions in the pattern. In an aspect, a plurality of pressure measurements are made in a pre-determined pattern on the skin and the pressure value is calculated by identifying the pressure value associated with a pre-determined position within the pattern and subtracting the largest pressure value made at the other positions in the pattern. In an aspect, a pressure value may be calculated from a portion of a set of pressure values generated by a plurality of pressure measurements at a single location and pressure value calculated as the largest difference between the average and a single pressure value of the same set. In an aspect, a pressure value may be calculated as a ratio of the largest pressure value to the smallest pressure value within a set of pressure values.

In an aspect, the methods provided herein are based on measured pressure values on a patient's skin. In an aspect, the methods provided herein are applied from the time a patient is admitted to a care facility, until the patient is discharged from the care facility.

In an aspect, a wound is a pressure ulcer. In one aspect, a pressure ulcer is a pressure ulcer resulting from an extended period of use of a medical device such as, for example, a mask, a tubing, or a strap. In an aspect, a wound is a diabetic foot ulcer. In an aspect, a wound is a vascular ulcer. In an aspect, a wound is a burn wound.

Methods of Reducing Incidence of Tissue Damage

In one aspect, the present disclosure provides for, and includes, a method of reducing incidence of tissue damage in patients admitted to a care facility, the method comprising the steps of: evaluating a patient for a risk of tissue damage upon admission to the care facility, where the evaluating step comprises taking a pressure measurement of the patient at one or more body locations at risk of wound development, and determining an average pressure value of the pressure measurements; administering an intervention of level-0 if the average pressure value is below a first threshold, and administering an intervention of level-N if the average pressure value exceeds the first threshold, where N is an integer and N has a value of 1 or greater. In an aspect, the incidence of ulcers in patients in the care facility is reduced to less than 1 in 100, less than 1 in 200, less than 1 in 300, less than 1 in 400, less than 1 in 500, less than 1 in 600, less than 1 in 700, less than 1 in 800, less than 1 in 900, or less than 1 in 1000.

In an aspect, a care facility is selected from the group consisting of a hospital, a recovery facility, an assisted living facility, a residential care facility, a nursing home, a long-term care facility, a continuing care community, and an independent living community. In an aspect, a care facility may be a home or other residence of the patient, whereupon the "admit" step will be a first evaluation of a patient at their home by a nurse or other caregiver. In one aspect, the schedule of interventions and evaluation intervals used in a home setting may be different than the corresponding interventions and intervals used at a hospital.

In an aspect, the methods disclosed herein comprise evaluating a newly admitted patient for a risk of tissue damage. In an aspect, evaluating a patient comprises performing a visual assessment. In one aspect, the visual assessment is performed in accordance with the guidelines of the National Pressure Ulcer Advisory Panel (NPUAP).

In one aspect, evaluating a patient comprises performing a risk assessment. In an aspect, the risk assessment is performed in accordance with a test selected from the group consisting of the Braden Scale, the Gosnell Scale, the Norton Scale, and the Waterlow Scale. In an aspect, evaluating a patient further comprises performing an assessment using one or more objective measurements selected from the group consisting of: sub-epidermal moisture, bioimpedance, blood perfusion, biocapacitance, blood oxygenation, spectral imaging, PET imaging, capillary pressure, magnetic resonance imaging, thermal imaging, ultrasound imaging, transcutaneous water loss, and detection of interleukin-1 alpha presence at one or more anatomic site of interest.

FIGS. 7A-D illustrate locations of tissue injury risk in circles for patients in different positions. In an aspect, one or more body locations at risk of developing pressure injuries is selected from the group consisting of the back of the head, shoulder, base of spine, buttocks, heel, toes, elbow, ear, hip, thigh, leg, rib cage, and knees. In an aspect, one or more body locations at risk of developing tissue injury is selected from the group consisting of sternum, a *sacrum*, a heel, a *scapula* (os *latum scapularum*), an elbow, an ear, and other fleshy tissues over a bony prominence of a patient.

In an aspect, a newly admitted patient receives an intake evaluation that includes one or more of a visual examination of a portion of the patient's skin, completion of at least a portion of a risk assessment protocol that evaluates one or more of nutrition, mobility, physical activity, physical strength, and ability to communicate, and pressure measurements are taken in one or more locations on the patient's skin. In an aspect, a pressure measurement scan includes obtaining a plurality of pressure measurements at a single "location" on the patient's skin. In one aspect, "location" is considered as an area rather than a single point such that pressure measurements may be made at spatially separated points within the location. For example, a heel location includes the medial, lateral, and posterior surfaces around the heel as well as the posterior portion of the sole of that foot. In an aspect, a pressure measurement scan includes obtaining a pressure measurement at a single location on the patient's skin. In an aspect, a pressure measurement scan includes obtaining a pressure measurement at multiple locations on the patient's skin. In an aspect, a pressure measurement scan includes obtaining a plurality of pressure measurements at multiple locations on the patient's skin. In an aspect, evaluating a patient comprises determining an average pressure value of a pressure measurement. In an aspect, evaluating a patient comprises determining an average pressure value of a plurality of pressure measurements.

Methods of Assigning Patients to Risk Categories

In one aspect, once the evaluation step is complete, a determination is made as to whether the patient's readings are abnormal, i.e., whether the combination of the results of the various elements of the evaluation indicate that the patient has, or is at risk of developing, further wound tissue damage. Each element of the evaluation may have an individual criterion for level of risk, for example a scoring system with threshold value that indicates an unacceptable risk.

In an aspect, an intervention of level-0 is administered if the average pressure value is below or equal to a first threshold. In an aspect, an intervention of level-N is administered if the average pressure value is above a first threshold. In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, an average pressure value above a first threshold value is an indication of a patient at risk of developing a pressure ulcer or tissue damage.

In an aspect, if the patient is determined to be at an acceptable level of risk, the lowest level of intervention is implemented, designated herein as "level-zero" or "level-0", and the patient will be re-assessed using at least the pressure measurement protocol at a frequency, or conversely a time interval, associated with level-0. In an aspect, a level-0 intervention is administered if the average pressure value is below a threshold.

In one aspect, if the patient is determined to have abnormal readings, then a higher level of intervention is implemented. In an aspect, there is a defined hierarchy of intervention levels, with each level implementing a more intensive intervention than the next-lower level. In an aspect, each level also has a defined monitoring interval or frequency indicating how often a set of pressure measurements should be made, where higher levels will generally have shorter intervals. In an aspect, the process has been defined by the hospital, or other administering organization, to step up one level to a level-1 intervention at this point. In another aspect, a level-2 or higher level of intervention can be implemented. The process now enters a new loop where the patient will now be monitored at a level-N frequency where N is in the range of 1 to n, n being the highest defined level of intervention and monitoring. In an aspect, a level-N intervention is administered if the average pressure value is above a threshold. In an aspect, the level-N intervention is anatomy-specific.

In an aspect, pressure measurements of a body location identified as having possible damage in the initial set of pressure measurements are obtained at a first time interval. In an aspect, pressure measurements of all other body locations selected for monitoring are obtained at a second time interval that is longer than the first time interval. In an aspect, the values of the first and second time intervals are different depending on the risk category to which the patient has been assigned. For example, a high-risk patient will have a first time interval of 4 hours and a second time interval of 1 day while an at-risk patient will have a first time interval of 1 day and a second time interval of 1 week. In an aspect, the time interval may be event-based, for example upon a change of attending staff or shift change, rather than strictly based on time. In general, body locations that have elevated pressure values are scanned more often than other body locations that are monitored but having normal pressure values in previous pressure measurement sessions.

In an aspect, the interval at which pressure measurements are taken is determined by the pressure value from the prior pressure measurement session. For example, a body location that had a pressure value greater than or equal to a first threshold in a previous measurement session is performed at a first time interval, while a pressure measurement is performed at a second time interval that is shorter than the first time interval when the prior pressure value at a body location was greater than or equal to a second threshold that is higher than the first threshold.

Methods of Assigning a Patient to a Risk Category

In one aspect, the present disclosure provides for, and includes, a method of assigning a patient in a care facility to a risk category selected from a plurality of risk categories, the method comprising the steps of: taking an initial pressure measurement of one or more locations of the body selected for monitoring; determining an average pressure value of the pressure measurement; and assigning the patient to a risk category selected from the plurality of risk categories, wherein the assigning is based partially on the average pressure value of the pressure measurement.

In one aspect, the risk level of the patient is determined entirely by pressure measurements. In one aspect, the risk level of the patient is determined entirely by visual examination of the patient. In one aspect, the risk level of the patient is determined entirely by performing a risk assessment protocol on the patient. In one aspect, the risk level of the patient is determined by pressure measurements and visual examination of the patient. In one aspect, the risk level of the patient is determined by performing a risk assessment protocol on the patient and a visual examination of the patient. In one aspect, the risk level of the patient is determined by pressure measurements and performing a risk assessment protocol on the patient. In one aspect, the risk level of the patient is determined by pressure measurements, performing a risk assessment protocol on the patient and a visual examination of the patient. In an aspect, there is a protocol to combine the criteria to generate a composite parameter that can be used to select a level of intervention.

In an aspect, the patient is assigned to a risk category selected from a plurality of risk categories. In an aspect, the risk categories comprise at-risk and high-risk categories. In an aspect, the risk categories comprise low-risk, and high-risk categories. In an aspect, the risk categories comprise low-risk, at-risk, and high-risk categories. In an aspect, there are 1, 2, 3, 4, 5, 6, 7, 8, 9, or 10 risk categories. In an aspect, a risk category is associated with a corresponding level of care. In an aspect, a risk category is associated with a corresponding level of intervention. In an aspect, a risk category is associated with a corresponding frequency of subsequent pressure measurements.

In an aspect, the patient is assigned to a risk category based on the average pressure value. In an aspect, the patient is assigned to a risk category based on the absolute average pressure value. In an aspect, the patient is assigned to a risk category by comparing the average pressure value to a threshold value. In an aspect, the patient is assigned to a risk category by comparing the average pressure value to a maximum intensity value. In an aspect, the assignment is based solely on the largest initial pressure value found during the initial pressure measurement scan.

Methods of Assigning Patients to Care Levels and Intervention Levels

In an aspect, the present disclosure provides for, and includes, a method of stratifying a plurality of patients in a care facility based on care levels, the method comprising the steps of: taking a pressure measurement of a patient in the plurality of patients at one or more body locations selected for monitoring, determining an average pressure value of the pressure measurement of the patient, determining a care level of N care levels that corresponds to the average pressure value; and assigning the care level to the patient; and arranging the patient of the plurality of patients into groups based on each of the patient's assigned care levels.

In an aspect, the patient is assigned to a care level based on the average pressure value. In an aspect, the patient is assigned to a care level of N care levels that corresponds to the average pressure value. In an aspect, there are 1, 2, 3, 4, 5, 6, 7, 8, 9, or 10 care levels. In an aspect, each of the N care levels corresponds to a range of average pressure values. In an aspect, a care level is associated with a corresponding level of intervention. In an aspect, a care level is associated with a corresponding frequency of subsequent pressure measurements. In an aspect, a plurality of patients are grouped and arranged according to their assigned care levels. In an aspect, a plurality of patients are grouped such that patients within a group are assigned to the same care level. In an aspect, a plurality of patients are grouped such that patients within a group are given the same interventions.

In one aspect, the present disclosure provides methods for identifying and providing an appropriate level of care to a patient in a care facility, the method comprising the steps of: taking a plurality of pressure measurements of the patient at one or more body locations; determining an average pressure value of the pressure measurement of the patient; providing one or more anatomy-specific interventions based on the average pressure value; increasing the level of anatomy-specific interventions based on an increase in the average pressure value; and decreasing the level of anatomy-specific interventions based on a decrease in the average pressure value.

In an aspect, the patient is assigned to a care level based on the average pressure value. In an aspect, the patient is assigned to a care level of N care levels that corresponds to the average pressure value. In an aspect, there are 1, 2, 3, 4, 5, 6, 7, 8, 9, or 10 care levels. In an aspect, each of the N care levels corresponds to a range of average pressure values. In an aspect, a care level is associated with a corresponding level of intervention. In an aspect, a care level is associated with a corresponding frequency of subsequent pressure measurements.

In an aspect, the patient's history is evaluated to determine whether their condition is improving. If the patient's condition is improving, for example as evidenced by a decreasing average pressure value, then the intervention level is decreased. In an aspect, the current level of intervention continues to be implemented until the average pressure value drops below the threshold. In an aspect, the level of intervention may be reduced based on the magnitude of the average pressure value as the average pressure value trends downward. If the patient's condition is worsening, for example as evidenced by an increasing average pressure value, then the intervention level is increased. In an aspect, the current level of intervention continues to be implemented until the average pressure value rises above the threshold. In an aspect, the level of intervention may be increased based on the magnitude of the average pressure value as the average pressure value trends upward.

In one aspect, if the patient does not show improvement, the process branches to an increase in the level of intervention provided that the skin is not broken, i.e., an open wound has not developed. If an open wound has developed, pressure measurements will now be made around the periphery of the open wound to map inflammation or other precursor indication of the wound enlarging. The open wound itself is treated and its periphery monitored until the wound closes.

In one aspect, an anatomy-specific intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the decision to implement an intervention for a particular body site, or a general intervention such as a high-spec mattress, is based on the pressure value found for that site in the pressure measurement scan. If the pressure value is less than a predetermined threshold, no intervention is required. If the pressure value is greater than the predetermined threshold, then an intervention is selected and implemented based partially on the body location and partially on the average pressure value for that body location. The predetermined threshold for whether or not to select and implement an intervention may be higher or lower than the threshold for determination that there is possible damage at the body location.

Methods of Managing Care

In an aspect, the present disclosure provides a method of managing care of a patient, the method comprising the steps of: taking a first set of pressure measurements at one or more body locations selected for monitoring upon admission to a care facility, determining a first average pressure value of each of the first set of pressure measurements, setting an intervention level to N=1 if one of the average pressure value of the first set of pressure measurements is above a first threshold, implementing a level-N intervention for each of the one or more body locations having an average pressure value above a first threshold, taking subsequent sets of pressure measurements at each of the one or more body locations at a level-N frequency, and determining new average pressure values for each of the one or more body locations.

In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein. It will be understood that a threshold is not limited by design, but rather, one of ordinary skill in the art would be capable of choosing a predetermined value based on a given unit of pressure value. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, N ranges from 1 to 50, such as from 1 to 2, from 1 to 3, from 1 to 4, from 1 to 5, from 1 to 6, from 1 to 7, from 1 to 8, from 1 to 9, from 1 to 10, from 1 to 15, from 1 to 20, from 1 to 25, from 1 to 30, from 1 to 35, from 1 to 40, or from 1 to 45. In one aspect, N is determined by the amount by which the first average pressure value exceeds the first threshold. In one aspect, a level-N intervention corresponds to a range of average pressure values. In an aspect, a level-N intervention is associated with a corresponding anatomy-specific intervention. In an aspect, a level-N intervention is associated with a corresponding frequency of subsequent pressure measurements. In an aspect, a level-N intervention is selected from the group consisting of a heel boot, a barrier cream, neuromuscular stimulation, a topical cream, therapeutic ultrasound, shockwave therapy, a 30-degree wedge, a composite dressing, a hybrid mattress, and a dynamic mattress, a support surface, a silicone pad, a low-friction sheet cover, and a low-friction padded mattress surface.

In an aspect, care of a patient is discharge or transfer from the care facility. In an aspect, the condition of the patient upon discharge or transfer is documented. In an aspect, a final set of pressure measurements at one or more locations on the patient's body is taken before discharge or transfer. In one aspect, a final set of pressure measurements at one or more locations on the patient's body is taken. In an aspect, these locations are one or more body locations selected for monitoring. In an aspect, these locations include areas that were not receiving an intervention and were not previously identified as at risk. In an aspect, this information is provided to the receiving caregiver.

Methods of Identifying and Treating a Patient at Risk of Tissue Damage

In an aspect, the present disclosure provides for, and includes, a method of identifying and treating a patient at risk of tissue damage. In an aspect, the method comprises the steps of: evaluating a patient for a risk of tissue damage upon admission to a care facility, wherein the evaluating step comprises taking a first plurality of pressure measurements in the patient, determining a first average pressure value of the first plurality of pressure measurements, administering a first intervention of level-0 if the first average pressure value is below or equal to a first threshold, and administering a first intervention of level-N if the first average pressure value is above the first threshold, where N is an integer and N has a value of 1 or greater. In an aspect, the first average pressure value is determined from a subset of the first plurality of pressure measurements.

FIGS. 7A-D illustrate locations of tissue injury risk in circles for patients in different positions. In an aspect, a first plurality of pressure measurements is taken at or around one or more body locations selected from the group consisting of sternum, a *sacrum*, a heel, a *scapula* (os *latum scapularum*), an elbow, an ear, and other fleshy tissues over a bony prominence of a patient. In an aspect, a first plurality of pressure measurements is taken at and around one or more anatomical sites in long-term contact with a medical device, an anatomical site is selected from the group consisting of a cheek, a nose, a chest, a stomach, and a lower abdomen area. In an aspect, a first plurality of pressure measurements is separated into sub-groups for analysis based on the general location at which a measurement is taken. In an aspect, the average pressure value is determined from a subset of the first plurality of pressure measurements. In one aspect, a first plurality of pressure measurements is taken at locations located on one or more concentric circles centered around an anatomical site. In an aspect, a first plurality of pressure measurements is taken at locations located on a straight line at approximately equidistance from an anatomical site.

In one aspect, a first pressure difference is determined by the difference between the maximum pressure value and the minimum pressure value from the first plurality of pressure measurements collected. In an aspect, a first pressure difference is determined by the difference between the maximum average pressure value of measurements taken at one location and the minimum average pressure value of measurements taken at a second location. In an aspect, a first pressure difference is determined by the difference between the maximum average pressure value of measurements taken at one location and the absolute minimum pressure value of measurements taken at a second location. In an aspect, a first pressure difference is determined by the difference between the absolute maximum pressure value of measurements taken at one location and the minimum average pressure value of measurements taken at a second location. In an aspect, a first pressure difference is determined by the difference between the maximum average pressure value of measurements and the minimum average pressure value of measurements taken at different times at the same location. In one aspect, a first pressure value is determined for a portion of a first plurality of pressure measurements made up of a sub-group as defined by location taken. In an aspect, an average pressure value at a location is obtained from two, three, four, five, six, seven, eight, nine, ten, or more than ten pressure values measured at that location. In one aspect, a first pressure difference is determined by the difference between average pressure values derived from measurements taken at two bisymmetric locations with respect to a centerline. In an aspect, a first pressure difference is the difference between absolute pressure values derived from measurements taken at two bisymmetric locations with respect to a centerline. In an aspect, a first pressure difference is the difference between an pressure value measured at one location on the left side of the body, e.g., left heel, and the same location on the right side of the body, e.g., right heel.

In an aspect, a pressure value may be calculated from a plurality of pressure measurements made at a certain location, or in close proximity around a specific location, in a plurality of methods disclosed herein. In an aspect, a plurality of pressure measurements are made in a pre-determined pattern on the skin and the pressure value is calculated by subtracting the pressure value associated with a pre-determined position within the pattern from the largest pressure value made at the other positions in the pattern. In an aspect, a plurality of pressure measurements are made in a pre-determined pattern on the skin and the pressure value is calculated by identifying the pressure value associated with a pre-determined position within the pattern and subtracting the largest pressure value made at the other positions in the pattern. In an aspect, an average pressure value may be calculated from a portion of a set of pressure values generated by a plurality of pressure measurements at a single location and an average pressure value calculated as the largest difference between the average and a single pressure value of the same set. In an aspect, an average pressure value may be calculated as a ratio of the largest pressure value to the smallest pressure value within a set of pressure values.

In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein. It will be understood that a threshold is not limited by design, but rather, one of ordinary skill in the art would be capable of choosing a predetermined value based on a given unit of pressure value. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, N ranges from 1 to 50, such as from 1 to 2, from 1 to 3, from 1 to 4, from 1 to 5, from 1 to 6, from 1 to 7, from 1 to 8, from 1 to 9, from 1 to 10, from 1 to 15, from 1 to 20, from 1 to 25, from 1 to 30, from 1 to 35, from 1 to 40, or from 1 to 45.

In one aspect, N is determined by the amount by which the first average pressure value exceeds the first threshold. In an aspect, the amount by which a threshold established for (N+1) exceeds the first threshold is greater than the amount by which a threshold established for N exceeds the first threshold. In one aspect, the amount by which a threshold established for (N−1) exceeds the first threshold is less than the amount by which a threshold established for N exceeds the first threshold. In an aspect, the value of threshold established for (N+1) is greater than the value of the threshold established for N. In an aspect, the value of threshold established for N is greater than the value of the threshold established for (N−1).

Selection of Intervention Levels

In an aspect, a level-1 (N=1) intervention is applied to a patient having an average pressure value exceeding the threshold by not more than 100% of the threshold value, such as not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-1 intervention is applied to a location at which a measurement was made.

In an aspect, a level-2 (N=2) intervention is applied to a patient having an average pressure value exceeding the threshold by not more than 150% of the threshold value, such as not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-2 intervention is applied to a location at which a measurement was made.

In one aspect, a level-3 (N=3) intervention is applied to a patient having an average pressure value exceeding the threshold by not more than 200% of the threshold value, such as not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-3 intervention is applied to a location at which a measurement was made.

In one aspect, a level-4 (N=4) intervention is applied to a patient having an average pressure value exceeding the threshold by not more than 250% of the threshold value, such as not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-4 intervention is applied to a location at which a measurement was made.

In one aspect, a level-5 (N=5) intervention is applied to a patient having an average pressure value exceeding the threshold by not more than 300% of the threshold value, such as not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-5 intervention is applied to a location at which a measurement was made.

In one aspect, a level-6 (N=6) intervention is applied to a patient having an average pressure value exceeding the threshold by not more than 350% of the threshold value, such as not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-6 intervention is applied to a location at which a measurement was made.

In one aspect, a level-7 (N=7) intervention is applied to a patient having an average pressure value exceeding the threshold by not more than 400% of the threshold value, such as not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-7 intervention is applied to a location at which a measurement was made.

In one aspect, a level-8 (N=8) intervention is applied to a patient having an average pressure value exceeding the threshold by not more than 450% of the threshold value, such as not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-8 intervention is applied to a location at which a measurement was made.

In one aspect, a level-9 (N=9) intervention is applied to a patient having an average pressure value exceeding the threshold by not more than 500% of the threshold value, such as not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-9 intervention is applied to a location at which a measurement was made.

In one aspect, a level-10 (N=10) intervention is applied to a patient having an average pressure value exceeding the threshold by not more than 550% of the threshold value, such as not more than 545%, not more than 540%, not more than 535%, not more than 530%, not more than 525%, not more than 520%, not more than 515%, not more than 510%, not more than 505%, not more than 500%, not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-10 intervention is applied to a location at which a measurement was made.

In one aspect, a level-N intervention is more intensive than a level-0 intervention. In an aspect, a level-(N+1) intervention is more intensive than a level-N intervention. In one aspect, a level-(N−1) intervention is less intensive than a level-N intervention.

Methods of Identifying and Treating a Patient at Risk of Tissue Damage—Subsequent Imaging In an aspect, the present disclosure further provides for, and includes, taking a second plurality of pressure measurements in the patient at a first pre-determined frequency corresponding to the administered intervention level, determining a second average pressure value from the second plurality of pressure measurements, determining whether the second average pressure value exceeds a second threshold, continuing to administer the first intervention if the second average pressure value does not exceed the second threshold, continuing to take a plurality of pressure measurements at the first pre-determined frequency if the second average pressure value does not exceed the second threshold, administering a second intervention of level-M if the second average pressure value exceeds the second threshold, where M is an integer and M is greater than N, and taking a plurality of pressure measurements at a second pre-determined frequency corresponding to level-M if the second average pressure value exceeds the second threshold.

In one aspect, a pre-determined frequency is selected from the group consisting of at least once every 72 hours, at least once every 48 hours, at least once every 24 hours, at least once every 12 hours, at least once every 8 hours, at least once every 6 hours, at least once every 4 hours, at least once every 3 hours, at least once every 2 hours, at least once every hour, and at least once every half an hour.

In an aspect, a second plurality of pressure measurements is taken at or around one or more body locations selected from the group consisting of sternum, a *sacrum*, a heel, a *scapula* (os *latum scapularum*), an elbow, an ear, and other fleshy tissues over a bony prominence of a patient. In an aspect, a second plurality of pressure measurements is taken at and around one or more anatomical sites in long-term contact with a medical device, an anatomical site is selected from the group consisting of a cheek, a nose, a chest, a stomach, and a lower abdomen area. In an aspect, a second plurality of pressure measurements is separated into subgroups for analysis based on the general location at which a measurement is taken. In an aspect, the second average pressure value is determined from a subset of the second plurality of pressure measurements. In one aspect, a second plurality of pressure measurements is taken at locations located on one or more concentric circles centered around an anatomical site. In an aspect, a second plurality of pressure measurements is taken at locations located on a straight line at approximately equidistance from an anatomical site.

In one aspect, a second pressure difference is determined by the difference between the maximum pressure value and the minimum pressure value from the second plurality of pressure measurements collected. In an aspect, a second pressure difference is determined by the difference between the maximum average pressure value of measurements taken at one location and the minimum pressure value of measurements taken at a second location. In an aspect, a second pressure difference is determined by the difference between the maximum average pressure value of measurements and the minimum pressure value of measurements taken at the same location. In one aspect, a second average pressure value is determined for a portion of a second plurality of pressure measurements made up of a sub-group as defined by location taken. In an aspect, a second average pressure value at a location is obtained from two, three, four, five, six, seven, eight, nine, ten, or more than ten pressure values measured at that location. In one aspect, a second pressure difference is determined by the difference between average pressure values derived from measurements taken at two bisymmetric locations with respect to a centerline. In an aspect, a second plurality of pressure measurements are made at the same locations where a first plurality of pressure measurements were taken. In one aspect, a second plurality of pressure measurements are made at some of the same locations where a first plurality of pressure measurements were taken. In an aspect, a second plurality of pressure measurements are made near the locations where a first plurality of pressure measurements were taken. In one aspect, a second plurality of pressure measurements are made at different locations than where a first plurality of pressure measurements were taken.

In an aspect, the second threshold is equal to the first threshold. In an aspect, a second threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a second threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a second threshold can be scaled by a factor or a multiple based on the values provided herein. In one aspect, a second threshold is equal to the first threshold. In an aspect, a second threshold can be greater than a first threshold. In one aspect, a second threshold can be less than a first threshold.

In an aspect, a second average pressure value can be 0.1-99.5% of the second threshold, such as 0.1-1%, 0.1-5%, 1-5%, 5-15%, 10-20%, 15-25%, 20-30%, 25-35%, 30-40%, 35-45%, 40-50%, 0.1-25%, 15-35%, 25-50%, 25-75%, 45-55%, 50-60%, 55-65%, 60-70%, 65-75%, 40-55%, 50-75%, 50-99.5%, 70-80%, 75%-85%, 80-90%, 85-95%, 90-99.5%, 65-85%, or 75-99.5% of the second threshold.

In an aspect, M ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In one aspect, M is determined by the amount by which the second pressure value exceeds the second threshold. In an aspect, the amount by which a threshold established for (M+1) exceeds the second threshold is greater than the amount by which a threshold established for M exceeds the second threshold. In one aspect, the amount by which a threshold established for (M−1) exceeds the second threshold is less than the amount by which a threshold established for M exceeds the second threshold. In an aspect, the value of threshold established for (M+1) is greater than the value of the threshold established for M. In an aspect, the value of threshold established for M is greater than the value of the threshold established for (M−1).

In an aspect, a level M intervention is chosen in accordance with the above "Selection of Intervention Levels" of this disclosure, replacing N with M.

In one aspect, the present disclosure further provides for, and includes, determining whether the second average pressure value is less than a third threshold, continuing to administer the first intervention if the second average pressure value is not less than the third threshold, continuing to take a plurality of pressure measurements at the first predetermined frequency if the second average pressure value is not less than the third threshold, administering a third intervention of level-L if the second average pressure value is less than the third threshold and if the first intervention is not of level-0, where L is an integer and L is less than N, and taking a plurality of pressure measurements at a pre-determined frequency corresponding to level-L if the second average pressure value is less than the third threshold.

In an aspect, L ranges from 0 to 50, such as from 0 to 3, from 0 to 4, from 0 to 5, from 0 to 6, from 0 to 7, from 0 to 8, from 0 to 9, from 0 to 10, from 0 to 15, from 0 to 20, from 0 to 25, from 0 to 30, from 0 to 35, from 0 to 40, or from 0 to 45.

In one aspect, L is determined by the amount by which the second average pressure value is less than the third threshold. In an aspect, the amount by which a threshold established for (L−1) is less than the third threshold is greater than the amount by which a threshold established for L is less than the third threshold. In one aspect, the amount by which a threshold established for (L+1) is less than the third threshold is less than the amount by which a threshold established for L is less than the third threshold. In an aspect, the value of threshold established for (L+1) is greater than the value of the threshold established for L. In an aspect, the value of threshold established for L is greater than the value of the threshold established for (L−1).

In an aspect, a third threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a third threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a third threshold can be scaled by a factor or a multiple based on the values provided herein. In one aspect, a third threshold is equal to the first threshold. In an aspect, a third threshold can be greater than a first threshold. In one aspect, a third threshold can be less than a first threshold. In one aspect, a third threshold is equal to the second threshold. In an aspect, a third threshold can be greater than a second threshold. In one aspect, a third threshold can be less than a second threshold.

In an aspect, a second average pressure value can be 0.1-99.5% of the third threshold, such as 0.1-1%, 0.1-5%, 1-5%, 5-15%, 10-20%, 15-25%, 20-30%, 25-35%, 30-40%, 35-45%, 40-50%, 0.1-25%, 15-35%, 25-50%, 25-75%, 45-55%, 50-60%, 55-65%, 60-70%, 65-75%, 40-55%, 50-75%, 50-99.5%, 70-80%, 75%-85%, 80-90%, 85-95%, 90-99.5%, 65-85%, or 75-99.5% of the third threshold.

In an aspect, a level L intervention is chosen in accordance with the above "Selection of Intervention Levels" of this disclosure, replacing N with L.

In an aspect, a level-N intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, a level-M intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, a level-L intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Methods of Slowing the Progression of Skin and Tissue Damage

In one aspect, the present disclosure provides for, and includes, a method of slowing the progression of skin and tissue damage in a patient in need thereof, the method comprising the steps of: identifying a current intervention of level-K received by the patient, take a plurality of pressure measurements in the patient, calculating an average pressure value from a portion of the plurality of pressure measurements, determining whether the average pressure value exceeds a first threshold, continuing to administer the current intervention if the average pressure value does not exceed the first threshold, continuing to take a plurality of pressure measurements at a pre-determined frequency corresponding to level-K if the average pressure value does not exceed the first threshold, administering a new intervention of level-N if the average pressure value exceeds the first threshold, where N has a value greater than K, and taking a plurality of pressure measurements at a pre-determined frequency corresponding to level-N if the average pressure value exceeds the first threshold.

In an aspect, a patient in need thereof is a patient experiencing a change of care, a change in mobility, a change in nutrition, a change in sensory perception, or a combination thereof. In one aspect, a patient in need thereof is a patient having developed an open wound. In an aspect, a patient in need thereof is a patient having recovered from an open wound. In one aspect, a patient in need thereof is a patient receiving surgery. In an aspect, a patient in need thereof is a patient recovering from surgery. In an aspect, a patient in need thereof is a patient receiving spinal analgesics or sacral analgesics during a surgery. In one aspect, a patient in need thereof is a patient receiving a surgery for a duration of four or more hours, such as five or more hours, six or more hours, seven or more hours, eight or more hours, nine or more hours, ten or more hours, eleven or more hours, or twelve or more hours. In an aspect, a surgery has a duration of one or more hours, such as two or more hours, or three or more hours.

In an aspect, a plurality of pressure measurements is taken at or around one or more body locations selected from the group consisting of sternum, a *sacrum*, a heel, a *scapula* (os *latum scapularum*), an elbow, an ear, and other fleshy tissues over a bony prominence of a patient. In an aspect, a plurality of pressure measurements is taken at and around one or more anatomical sites in long-term contact with a medical device, an anatomical site is selected from the group consisting of a cheek, a nose, a chest, a stomach, and a lower abdomen area. In an aspect, a plurality of pressure measurements is separated into sub-groups for analysis based on the general location at which a measurement is taken. In an aspect, the average pressure value is determined from a subset of the plurality of pressure measurements. In one aspect, a plurality of pressure measurements is taken at locations located on one or more concentric circles centered around an anatomical site. In an aspect, a plurality of pressure measurements is taken at locations located on a straight line at approximately equidistance from an anatomical site.

In an aspect, an average pressure value may be calculated from a plurality of pressure measurements made at a certain location, or in close proximity around a specific location, in a plurality of methods disclosed herein. In an aspect, a plurality of pressure measurements are made in a pre-determined pattern on the skin and the average pressure value is calculated by subtracting the pressure value associated with a pre-determined position within the pattern from the largest pressure value made at the other positions in the pattern. In an aspect, a plurality of pressure measurements are made in a pre-determined pattern on the skin and the average pressure value is calculated by identifying the pressure value associated with a pre-determined position within the pattern and subtracting the largest pressure value made at the other positions in the pattern. In an aspect, an average pressure value may be calculated from a portion of a set of pressure values generated by a plurality of pressure measurements at a single location and an average pressure value calculated as the largest difference between the average and a single pressure value of the same set. In an aspect, an average pressure value may be calculated as a ratio of the largest pressure value to the smallest pressure value within a set of pressure values.

In one aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein.

In an aspect, K ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In an aspect, K is determined by the amount by which the average pressure value exceeds the threshold. In an aspect, the amount by which an average pressure value exceeds a threshold established for (K+1) is greater than the amount by which an average pressure value exceeds a threshold established for K. In one aspect, the amount by which an average pressure value exceeds a threshold established for (K−1) is less than the amount by which an average pressure value exceeds a threshold established for K.

In an aspect, a level K intervention is chosen in accordance with the above "Selection of Intervention Levels" of this disclosure, replacing N with K.

In an aspect, the present disclosure further provides for, and includes, determining whether the average pressure value is less than a second threshold, administering a level-L intervention if the average pressure value is less than the second threshold, where L has a non-negative value less than K, and making a plurality of pressure measurements at a pre-determined frequency corresponding to level-L if the average pressure value is less than the second threshold.

In an aspect, the second threshold is equal to the first threshold. In an aspect, a second threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a second threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a second threshold can be scaled by a factor or a multiple based on the values provided herein. In one aspect, a second threshold is equal to the first threshold. In an aspect, a second threshold can be greater than a first threshold. In one aspect, a second threshold can be less than a first threshold.

In an aspect, L can be K−1, K−2, K−3, K−4, K−5, K−6, K−7, K−8, K−9, or K−10. In one aspect, L is K−1 if an average pressure value is 90-99.5% of the second threshold, such as 90-95%, 91-96%, 92-97%, 93-98%, 94-99%, or 95-99.5% of the second threshold, unless K−1 is less than 0, in which case L would be 0. In an aspect, L is K−2 if an average pressure value is 80-89.9% of the second threshold, such as 80-85%, 81-86%, 82-87%, 83-88%, 84-89%, or 85-89.9% of the second threshold, unless K−2 is less than 0, in which case L would be 0. In one aspect, L is K−3 if an average pressure value is 70-79.9% of the second threshold, such as 70-75%, 71-76%, 72-77%, 73-78%, 74-79%, or 75-79.9% of the second threshold, unless K−3 is less than 0, in which case L would be 0. In an aspect, L is K−4 if an average pressure value is 60-69.9% of the second threshold, such as 60-65%, 61-66%, 62-67%, 63-68%, 64-69%, or 65-69.9% of the second threshold, unless K−4 is less than 0, in which case L would be 0. In one aspect, L is K−5 if an average pressure value is 50-59.9% of the second threshold, such as 50-55%, 51-56%, 52-57%, 53-58%, 54-59%, or 55-59.9% of the second threshold, unless K−5 is less than 0, in which case L would be 0. In an aspect, L is K−6 if an average pressure value is 40-49.9% of the second threshold, such as 40-45%, 41-46%, 42-47%, 43-48%, 44-49%, or 45-49.9% of the second threshold, unless K−6 is less than 0, in which case L would be 0. In one aspect, L is K−7 if an average pressure value is 30-39.9% of the second threshold, such as 30-35%, 31-36%, 32-37%, 33-38%, 34-39%, or 35-39.9% of the second threshold, unless K-7 is less than 0, in which case L would be 0. In an aspect, L is K−8 if an average pressure value is 20-29.9% of the second threshold, such as 20-25%, 21-26%, 22-27%, 23-28%, 24-29%, or 25-29.9% of the second threshold, unless K−8 is less than 0, in which case L would be 0. In one aspect, L is K−9 if an average pressure value is 10-19.9% of the second threshold, such as 10-15%, 11-16%, 12-17%, 13-18%, 14-19%, or 15-19.9% of the second threshold, unless K−9 is less than 0, in which case L would be 0. In an aspect, L is K−10 if an average pressure value is 0.1-9.9% of the second threshold, such as 0.1-5%, 1-6%, 2-7%, 3-8%, 4-9%, or 5-9.9% of the second threshold, unless K−10 is less than 0, in which case L would be 0.

Methods of Identifying and Treating a Patient in Need of Intervention for Pressure Ulcer In an aspect, the present disclosure provides a method of identifying and treating a patient in need of an intervention for pressure ulcer, the method comprising the steps of: taking a plurality of pressure measurements at an anatomic site of the patient; determining an average pressure value of the plurality of pressure measurements; determining whether the average pressure value exceeds a threshold corresponding to level N, where N is greater than or equal to 2; administering the intervention for pressure ulcer to the anatomic site if the average pressure value exceeds the threshold; and taking a plurality of pressure measurements every two hours if the average pressure value exceeds the threshold.

In an aspect, the anatomical site is selected from the group consisting of a sternum, a *sacrum*, a heel, a *scapula* (os *latum scapularum*), an elbow, an ear, and other fleshy tissues over a bony prominence of a patient.

In an aspect, intervention for pressure ulcer is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the present disclosure provides for, and includes, a method of identifying and treating a patient in need of application of a barrier cream to the patient's heel, the method comprising the steps of: making a plurality of pressure measurements at the patient's heel, calculating an average pressure value from a portion of the plurality of pressure measurements, determining whether the average pressure value exceeds a threshold corresponding to level N, where N is greater than or equal to 2, administering a barrier cream to the patient's heel if the average pressure value exceeds the threshold, and making a plurality of pressure measurements every two hours if the average pressure value exceeds the threshold. In an aspect, a plurality of pressure measurements are made at least once every hour or at least once every half an hour if the average pressure value exceeds the threshold.

In one aspect, the present disclosure provides for, and includes, a method of identifying and treating a patient in need of application of a neuro-muscular stimulation to the patient's heel, the method comprising the steps of: making a plurality of pressure measurements at the patient's heel, calculating an average pressure value from a portion of the plurality of pressure measurements, determining whether the average pressure value exceeds a threshold corresponding to level N, where N is greater than or equal to 2, administering a neuro-muscular stimulation to the patient's heel if the average pressure value exceeds the threshold, and making a plurality of pressure measurements every hour if the average pressure value exceeds the threshold. In an aspect, a plurality of pressure measurements are made at least once every half an hour if the average pressure value exceeds the threshold.

In an aspect, the present disclosure provides for, and includes, a method of identifying and treating a patient in need of application of a topical cream to the patient's heel, the method comprising the steps of: making a plurality of pressure measurements at the patient's heel, calculating an average pressure value from a portion of the plurality of pressure measurements, determining whether the average pressure value exceeds a threshold corresponding to level N, where N is greater than or equal to 2, administering a topical cream to the patient's heel if the average pressure value exceeds the threshold, and making a plurality of pressure measurements every half an hour if the average pressure value exceeds the threshold.

In an aspect, the present disclosure provides for, and includes, a method of identifying and treating a patient in need of application of a heel boot to the patient's heel, the method comprising the steps of: making a plurality of pressure measurements at the patient's heel, calculating an average pressure value from a portion of the plurality of pressure measurements, determining whether the average pressure value exceeds a threshold corresponding to level N, where N is greater than or equal to 2, administering a heel boot to the patient's heel if the average pressure value exceeds the threshold, and making a plurality of pressure measurements every half an hour if the average pressure value exceeds the threshold.

In one aspect, the present disclosure provides for, and includes, a method of identifying and treating a patient in need of application of a barrier cream to the patient's *sacrum*, the method comprising the steps of: making a plurality of pressure measurements at the patient's *sacrum*, calculating an average pressure value from a portion of the plurality of pressure measurements, determining whether the average pressure value exceeds a threshold corresponding to level N, where N is greater than or equal to 2, administering a barrier cream to the patient's *sacrum* if the average pressure value exceeds the threshold, and making a plurality of pressure measurements every six hours if the average pressure value exceeds the threshold. In an aspect, a plurality of pressure measurements are made at least once every four hours, at least once every three hours, at least once every two hours, at least once an hour, or at least once every half an hour if the average pressure value exceeds the threshold.

In an aspect, the present disclosure provides for, and includes, a method of identifying and treating a patient in need of application of a neuro-muscular stimulation to the patient's *sacrum*, the method comprising the steps of: making a plurality of pressure measurements at the patient's *sacrum*, calculating an average pressure value from a portion of the plurality of pressure measurements, determining whether the average pressure value exceeds a threshold corresponding to level N, where N is greater than or equal to 2, administering a neuro-muscular stimulation to the patient's *sacrum* if the average pressure value exceeds the threshold, and making a plurality of pressure measurements every four hours if the average pressure value exceeds the threshold. In an aspect, a plurality of pressure measurements are made at least once every three hours, at least once every two hours, at least once an hour, or at least once every half an hour if the average pressure value exceeds the threshold.

In one aspect, the present disclosure provides for, and includes, a method of identifying and treating a patient in need of application of a topical cream to the patient's *sacrum*, the method comprising the steps of: making a plurality of pressure measurements at the patient's *sacrum*, calculating an average pressure value from a portion of the plurality of pressure measurements, determining whether the average pressure value exceeds a threshold corresponding to level N, where N is greater than or equal to 2, administering a topical cream to the patient's *sacrum* if the average pressure value exceeds the threshold, and making a plurality of pressure measurements every two hours if the average pressure value exceeds the threshold. In an aspect, a plurality of pressure measurements are made at least once an hour or at least once every half an hour if the average pressure value exceeds the threshold.

In one aspect, the present disclosure provides for, and includes, a method of identifying and treating a patient in need of application of therapeutic ultrasound, the method comprising the steps of: making a plurality of pressure measurements at an anatomic site of the patient, calculating an average pressure value from a portion of the plurality of pressure measurements, determining whether the average pressure value exceeds a threshold corresponding to level N, where N is greater than or equal to 2, administering therapeutic ultrasound to the anatomic site if the average pressure value exceeds the threshold, and making a plurality of pressure measurements every two hours if the average pressure value exceeds the threshold. In an aspect, an anatomical site is selected from the group consisting of a sternum, a *sacrum*, a heel, a *scapula* (os *latum scapularum*), an elbow, an ear, and other fleshy tissues over a bony prominence of a patient.

In one aspect, the present disclosure provides for, and includes, a method of identifying and treating a patient in need of application of shockwave therapy, the method comprising the steps of: making a plurality of pressure measurements at an anatomic site of the patient, calculating an average pressure value from a portion of the plurality of pressure measurements, determining whether the average pressure value exceeds a threshold corresponding to level N, where N is greater than or equal to 2, administering shockwave therapy to the anatomic site if the average pressure value exceeds the threshold, and making a plurality of pressure measurements every two hours if the average pressure value exceeds the threshold. In an aspect, an anatomical site is selected from the group consisting of a sternum, a *sacrum*, a heel, a *scapula* (os *latum scapularum*), an elbow, an ear, and other fleshy tissues over a bony prominence of a patient. In one aspect, shockwave therapy is provided via electromagnetic pulse or pressurized air.

In one aspect, the present disclosure provides for, and includes, a method of identifying and treating a patient in need of application of a 30-degree wedge, the method comprising the steps of: making a plurality of pressure measurements at an anatomic site of the patient, calculating an average pressure value from a portion of the plurality of pressure measurements, determining whether the average pressure value exceeds a threshold corresponding to level N, where N is greater than or equal to 2, administering a 30-degree wedge to the anatomic site if the average pressure value exceeds the threshold, and making a plurality of pressure measurements every two hours if the average pressure value exceeds the threshold. In an aspect, an anatomical site is selected from the group consisting of a sternum, a *sacrum*, a heel, a *scapula* (os *latum scapularum*), an elbow, an ear, and other fleshy tissues over a bony prominence of a patient.

In one aspect, the present disclosure provides for, and includes, a method of identifying and treating a patient in need of application of a composite dressing, the method comprising the steps of: making a plurality of pressure measurements at an anatomic site of the patient, calculating an average pressure value from a portion of the plurality of pressure measurements, determining whether the average pressure value exceeds a threshold corresponding to level N, where N is greater than or equal to 2, administering a composite dressing to the anatomic site if the average pressure value exceeds the threshold, and making a plurality of pressure measurements every two hours if the average pressure value exceeds the threshold. In an aspect, an anatomical site is selected from the group consisting of a sternum, a *sacrum*, a heel, a *scapula* (os *latum scapularum*), an elbow, an ear, and other fleshy tissues over a bony prominence of a patient.

In one aspect, the present disclosure provides for, and includes, a method of identifying and treating a patient in need of a hybrid mattress, the method comprising the steps of: making a plurality of pressure measurements at an anatomic site of the patient, calculating an average pressure value from a portion of the plurality of pressure measurements, determining whether the average pressure value exceeds a threshold corresponding to level N, where N is greater than or equal to 2, providing a hybrid mattress to support the patient if the average pressure value exceeds the threshold, and making a plurality of pressure measurements every two hours if the average pressure value exceeds the threshold. In an aspect, an anatomical site is selected from the group consisting of a sternum, a *sacrum*, a heel, a *scapula* (os *latum scapularum*), an elbow, an ear, and other fleshy tissues over a bony prominence of a patient.

In one aspect, the present disclosure provides for, and includes, a method of identifying and treating a patient in need of a dynamic mattress, the method comprising the steps of: making a plurality of pressure measurements at an anatomic site of the patient, calculating an average pressure value from a portion of the plurality of pressure measurements, determining whether the average pressure value exceeds a threshold corresponding to level N, where N is greater than or equal to 2, providing a dynamic mattress to support the patient if the average pressure value exceeds the threshold, and making a plurality of pressure measurements every two hours if the average pressure value exceeds the threshold. In an aspect, an anatomical site is selected from the group consisting of a sternum, a *sacrum*, a heel, a *scapula* (os *latum scapularum*), an elbow, an ear, and other fleshy tissues over a bony prominence of a patient.

In an aspect, the present disclosure provides for, and includes, a method of identifying and moving a bedridden patient in need thereof, the method comprising the steps of: providing a mobility sensor comprising an accelerometer and a gyro sensor; monitor frequency and range of mobilization of the patient; providing an alert when the mobility sensor does not sense a movement more than a quarter turn for a specified period of time; and moving the patient upon the alert.

In an aspect, the present disclosure further provides for, and includes, providing anatomy-specific intervention to an anatomical location of a patient identified as being damaged by a combination of a visual assessment and pressure measurements. In one aspect, an anatomy-specific intervention is provided to a common site for wound development selected from the group consisting of: toes, heels, a *sacrum*, a spine, elbows, shoulder blades, occiput, and ischial tuberosity. In an aspect, an anatomy-specific intervention is concurrently provided to a second common site for wound development selected from the group consisting of: toes, heels, a *sacrum*, a spine, elbows, shoulder blades, occiput, and ischial tuberosity. In one aspect, a first site receiving an anatomy-specific intervention is known to cause a development of a wound at a second site.

Comparison of Bisymmetric Pressure Measurements to Identify Damaged Tissue

In one aspect, the present disclosure provides for, and includes, a method of identifying damaged tissue, the method comprising the steps of: obtaining a first pressure measurement from a first location on a patient's skin; obtaining a second pressure measurement from a second location that is bisymmetric relative to the first location; determining an average pressure value of each of the first and second pressure measurements; determining the average pressure value from each of the first and second pressure measurements; determining a difference in the average pressure value between a first pressure measurement and a second pressure measurement; and determining that there is tissue damage at the first or second location if the difference in average pressure value exceeds a threshold value.

Figure 4A:
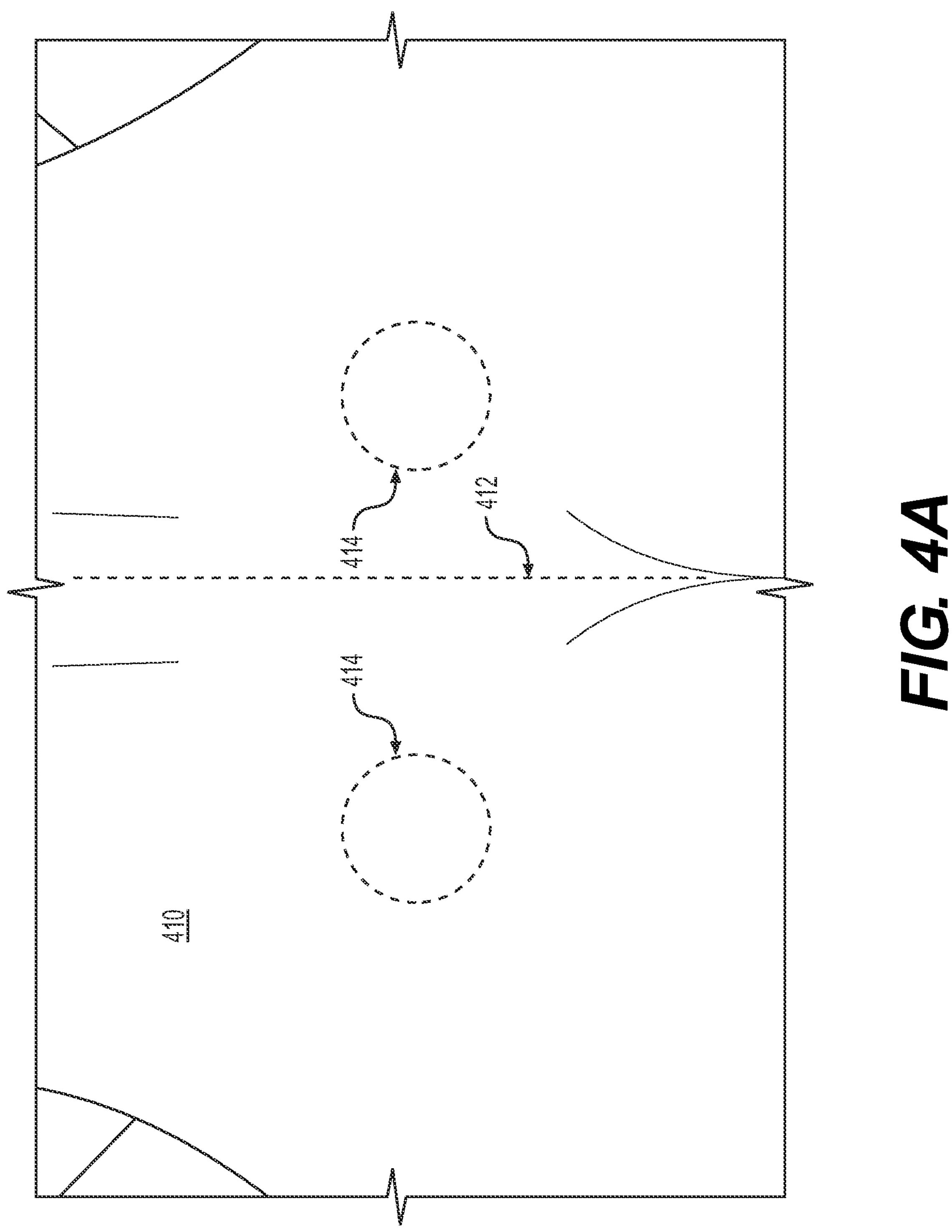
FIG. 4A provides an example of a pair of bisymmetric locations on a sacral region according to the present disclosure.

FIG. 4A depicts the sacral region of the back of a patient 410. A line of symmetry 412 can be drawn down the center of the back, dividing the back into left and right mirror images. Locations 414 are approximately the same distance from line of symmetry 412 and approximately at the same height and are, therefore, considered to be bisymmetric locations on the back of patient 410.

Figure 4B:
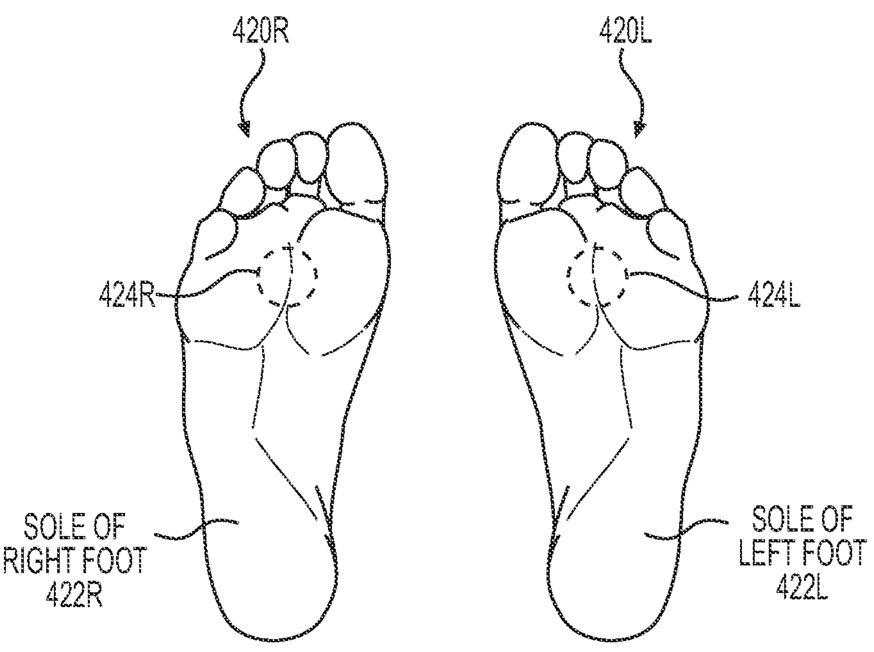
FIG. 4B provides an example of a pair of bisymmetric locations on the bottom side of both feet according to the present disclosure.

FIG. 4B depicts left foot 420L and right foot 420R of a patient 410, as seen if patient 410 were lying on the back on a bed (not shown) and an observer were standing at the foot of the bed. With respect to soles 422L and 422R of feet 420L and 420R, locations 424L and 424R are located at approximately equivalent locations, e.g. the same distance from the posterior surface, i.e. the heel, and the same distance from the medial side of respective foot 420L or 420R and are considered to be bisymmetric locations.

Figure 4C:
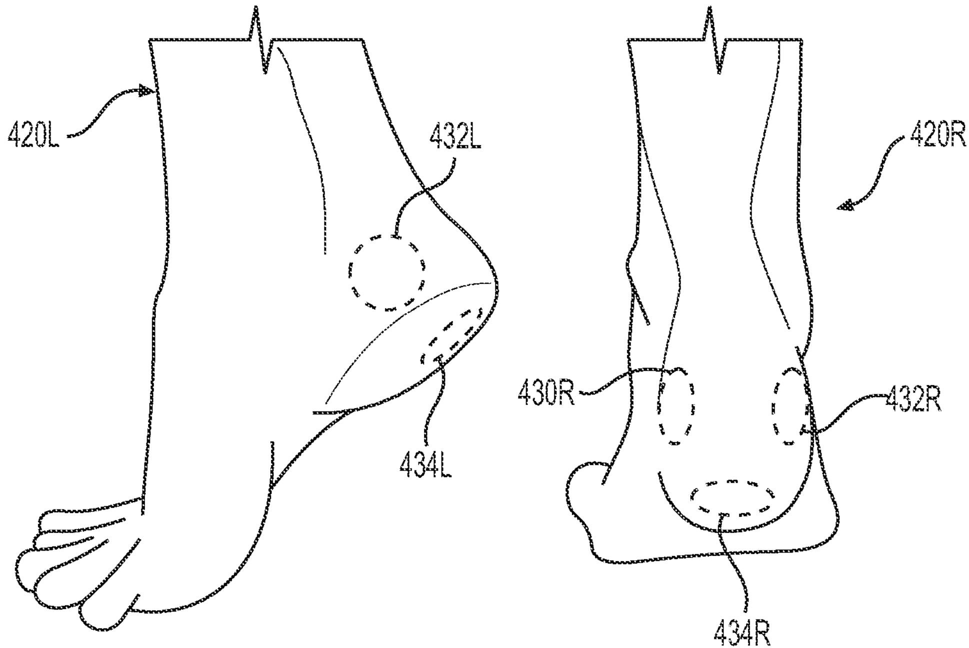
FIG. 4C provides an example of a pair of bisymmetric locations on the lateral sides and soles of both feet according to the present disclosure.

FIG. 4C depicts additional exemplary bisymmetric locations 432L and 432R located on the lateral sides of feet 420L and 420R, and bisymmetric locations 434L and 434R located on respective soles 422L and 422R of feet 420L and 420R. In an aspect, locations 432R and 430R are considered bisymmetric with respect to foot 420R when considered alone without reference to foot 420L.

Without being limited to a particular theory, comparison of pressure measurements taken at bisymmetric locations can compensate for an offset of readings of a particular patient from a population of patients. For example, a patient may be dehydrated on a particular day when measurements are being made. A comparison of the pressure value of healthy tissue from the same patient, while in a dehydrated condition, may be shifted from the pressure value of the same tissue at the same location when the patient is fully hydrated. If the tissue at one location is healthy while the tissue at the bisymmetric location is damaged, a comparison of the readings taken at the bisymmetric locations will exclude the "common mode" effect of dehydration variation at both locations and provide a more robust indication that tissue is damaged at one location.

Figure 6:
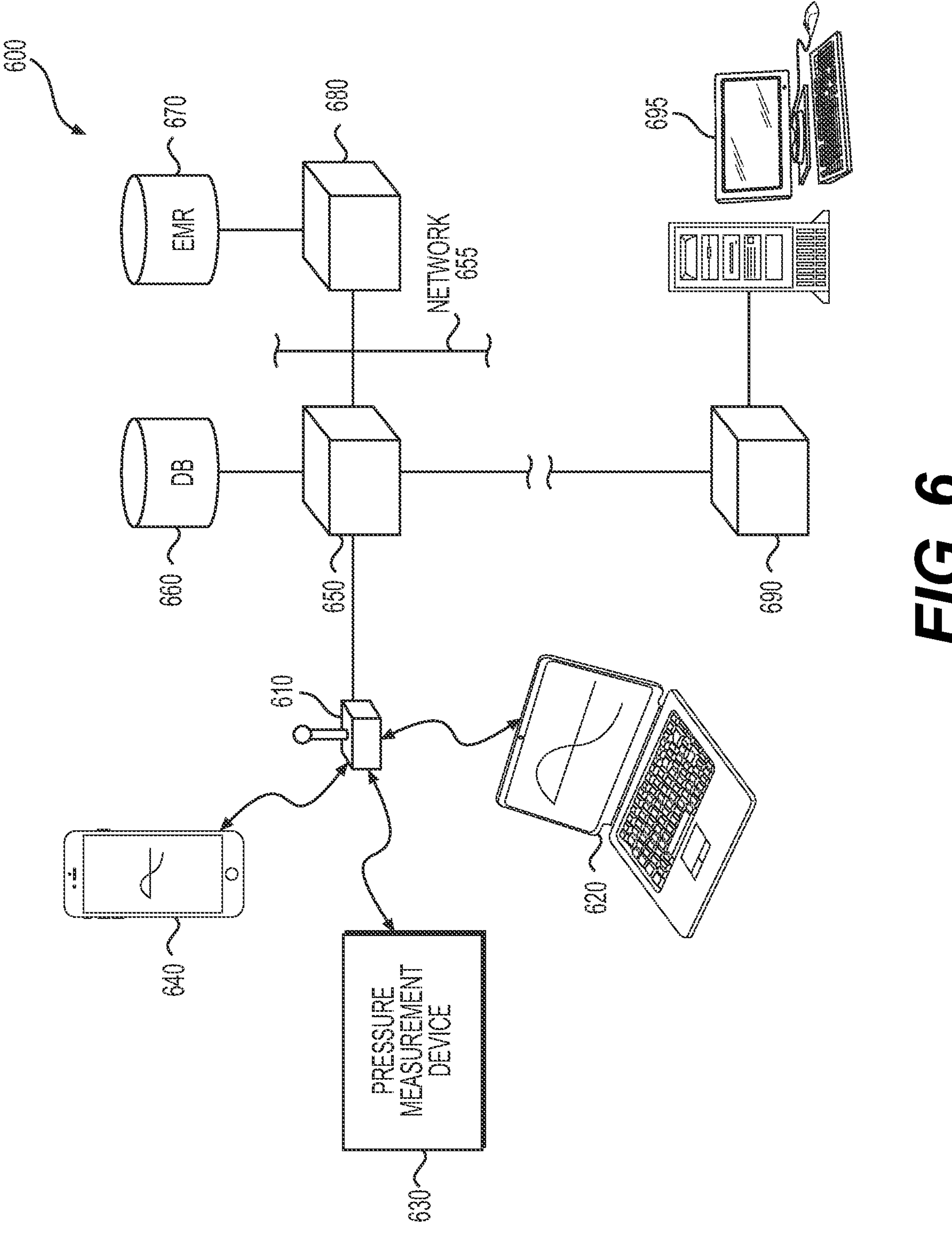
FIG. 6 depicts an integrated system for measurement, evaluation, storage, and transfer of pressure measurements, according to the present disclosure.
Figure 7A:
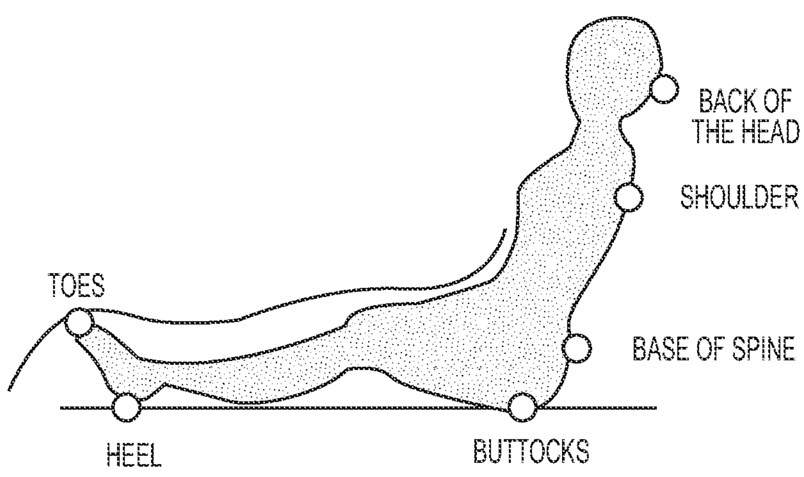
FIGS. 7A, 7B, 7C, and 7D illustrate various pressure points on a patient's body at different positions.
Figure 7B:
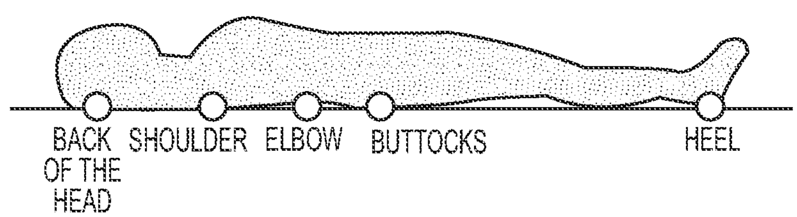
Figure 7C:
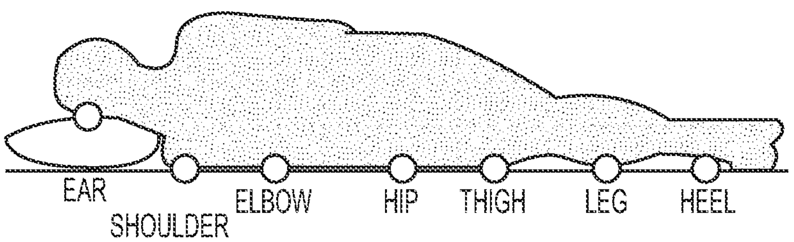
Figure 7D:
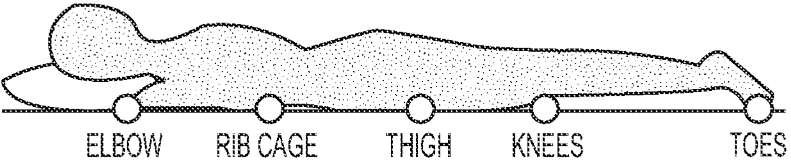

A pressure measurement apparatus 600 as provided in FIG. 6 may be used to take measurements at multiple locations, for example a first measurement at a first location and a second measurement at a second location that is bisymmetric relative to the first location. In an aspect, apparatus 600 comprises a processor that can be configured by instructions stored on a non-transitory computer-readable medium to determine a characteristic of the measurements taken at multiple locations or parameters associated with or derived from the measurements, for example one or more of a difference between, an average of, or a difference of each from a common average of pressure values respectively derived from multiple measurements. In one aspect, apparatus 600 comprises a display configured to show one or more parameters associated with the measurements, for example an average pressure value derived from measurements taken at two bisymmetric locations.

In one aspect, a difference between average pressure values is determined, where a difference that exceeds a predetermined threshold is indicative of tissue damage at one of the locations where the corresponding pressure measurements were taken. In an aspect, averages of pressure values obtained at each bisymmetric location are determined and compared. In one aspect, medians or modes of average pressure values obtained at each bisymmetric location are determined and compared. In an aspect, the damage is indicated to be at the location associated with the larger of the average pressure values. In one aspect, the damage is indicated to be at the location associated with the smaller of the average pressure values. In an aspect, determination of whether there is tissue damage comprises one or more of comparison of individual average pressure values with one or more predetermined ranges or thresholds and comparison of the difference with one or more predetermined ranges or thresholds. In an aspect, a predetermined range may be from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined range may be from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined range may be from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a predetermined threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined range or threshold can be scaled by a factor or a multiple based on the values provided herein. It will be understood that a predetermined value is not limited by design, but rather, one of ordinary skill in the art would be capable of choosing a predetermined value. In one aspect, ranges and thresholds of the present disclosure are varied according to the specific bisymmetric locations, the portion of a patient's body on which measurements are being made, or one or more characteristics of the patient such as age, height, weight, family history, ethnic group, and other physical characteristics or medical conditions.

One or more regions may be defined on a body. In an aspect, measurements made within a region are considered comparable to each other. A region may be defined as an area on the skin of the body wherein measurements may be taken at any point within the area. In an aspect, a region corresponds to an anatomical region (e.g., heel, ankle, lower back). In an aspect, a region may be defined as a set of two or more specific points relative to anatomical features wherein measurements are taken only at the specific points. In an aspect, a region may comprise a plurality of non-contiguous areas on the body. In an aspect, the set of specific locations may include points in multiple non-contiguous areas.

In an aspect, a region is defined by surface area. In an aspect, a region may be, for example, between 5 and 200 $cm^2$, between 5 and 100 $cm^2$, between 5 and 50 $cm^2$, or between 10 and 50 $cm^2$, between 10 and 25 $cm^2$, or between 5 and 25 $cm^2$.

In an aspect, measurements may be made in a specific pattern or portion thereof. In an aspect, the pattern of readings is made in a pattern with the target area of concern in the center. In an aspect, measurements are made in one or more circular patterns of increasing or decreasing size, T-shaped patterns, a set of specific locations, or randomly across a tissue or region. In an aspect, a pattern may be located on the body by defining a first measurement location of the pattern with respect to an anatomical feature with the remaining measurement locations of the pattern defined as offsets from the first measurement position.

In one aspect, the pressure measurement device of the present disclosure may further comprise a plurality of contact sensors on the same planar surface as, and surrounding, each of the receivers to ensure complete contact of the device to the skin surface. The plurality of contact sensors may be a plurality of pressure sensors, a plurality of light sensors, a plurality of temperature sensors, a plurality of pH sensors, a plurality of perspiration sensors, a plurality of ultrasonic sensors, a plurality of bone growth stimulator sensors, or a plurality of a combination of these sensors. In an aspect, the plurality of contact sensors may comprise four, five, six, seven, eight, nine, or ten or more contact sensors.

Figure 5A:
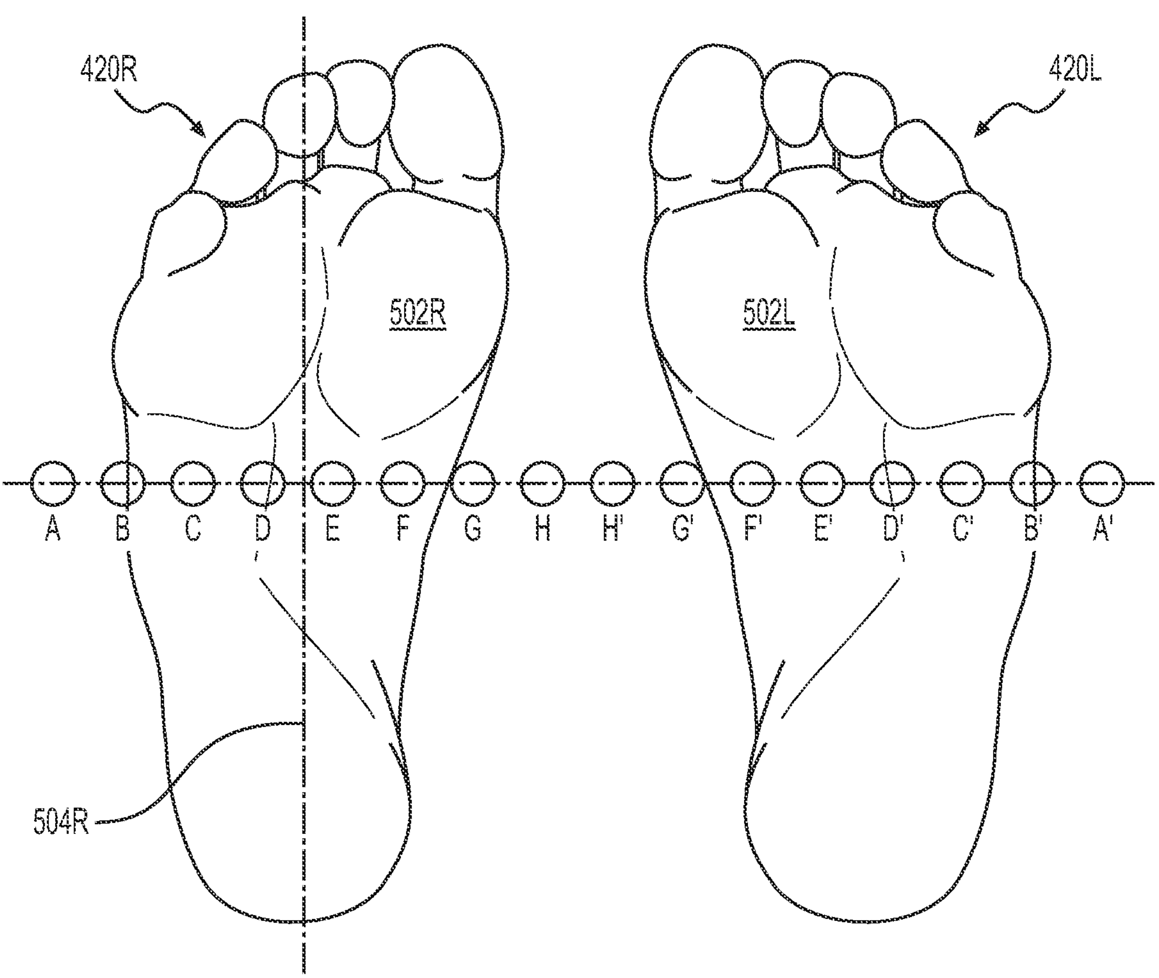
FIG. 5A illustrates locations on the left and right feet for pressure measurements according to the present disclosure.
Figure 5B:
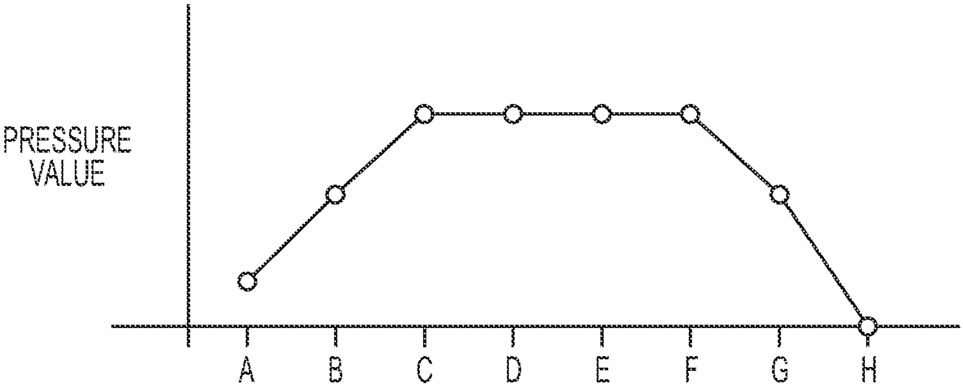
FIG. 5B is a plot of pressure values associated with known relative locations for identifying bisymmetric locations according to the present disclosure.

FIGS. 5A and 5B depict an example of how comparison of pressure values associated with measurements at known relative locations can identify bisymmetric locations, according to the present disclosure. In this example, an pressure measurement device 630 is presented at non-overlapping locations, marked "A" to "H" in FIG. 5A, across a contact area 502R of a right foot, e.g., 420R of FIG. 4C. The pressure values measured at each location are plotted in the graph of FIG. 5B. In this example, the pressure value of locations "A" and "H" are low or zero, reflecting the non-overlap of the pressure measurement device 630 with contact area 502R in those locations. The pressure values associated with locations "B" and "G" are higher, as the pressure measurement device 630 overlaps a portion of contact area 502R in those positions. The pressure values for locations C-D-E-F are higher and, in this example, approximately the same, indicating that the pressure measurement device 630 is completely within contact area 502R at those locations. In one aspect, a pressure measurement apparatus such as pressure measurement device 630 may determine that certain locations, for example locations "C" and "F," are bisymmetric with respect to a centerline 504R of right foot 420R. In an aspect, where a similar set of measurements is made at locations A'-H' on left foot 420L, a location on each foot 420L and 420R, for example locations E and E', may be determined to be approximately bisymmetric.

FIG. 6 depicts a schematic depiction of an integrated system 600 for measurement, evaluation, storage, and transfer of pressure measurements, according to the present disclosure. In this example, system 600 comprises an pressure measurement device 630 that comprises the capability to wirelessly communicate with a WiFi access point 610. Pressure measurement device 630 communicates with one or more of a pressure measurement application running on a server 650, an application running on a laptop computer 620, a smart phone 640, or other digital device. In one aspect, laptop computer 620 and smart phone 640 are carried by a user of pressure measurement device 630, for example a nurse, and an application provides feedback and information to the user. In an aspect, information received from pressure measurement device 630 for a patient is stored in a database 660. In one aspect, information received from pressure measurement device 630 is transferred over a network 655 to another server 680 that stores a portion of information in an electronic medical record (EMR) 670 of a patient. In one aspect, information from pressure measurement device 630 or retrieved from database 660 or EMR 670 is transferred to an external server 690 and then to a computer 695, for example a computer at the office of a doctor who is providing care for a patient.

Methods of Detecting Tissue Damage Before it is Visible

In one aspect, the present disclosure provides for, and includes, a method of detecting tissue damage before it is visible on a patient's skin, the method comprising the steps of: taking a plurality of pressure measurements at a location on the patient's skin at incremental times, determining an average pressure value from the each of the plurality of pressure measurements, calculating a slope between the latest pressure values and the immediately prior pressure values, comparing this slope to a threshold value, and determining that there is tissue damage if the derivative exceeds the threshold value. In an aspect, the method is performed at a plurality of locations.

In an aspect, the slope between the latest average pressure value and the immediately prior average pressure value is indicative of tissue damage. In an aspect, a positive slope between the latest average pressure value and the immediately prior average pressure value is indicative of worsening tissue damage. In an aspect, a positive slope between the latest average pressure value and the immediately prior average pressure value is indicative of a pressure ulcer forming.

In one aspect, the present disclosure provides for, and includes, a method of detecting tissue damage before it is visible on a patient's skin, the method comprising the steps of: taking a plurality of pressure measurements on the patient's skin at a plurality of locations at incremental times; determining an average pressure value from the each of the plurality of pressure measurements; calculating a difference value of the maximum average pressure value and the minimum average pressure value for each time; calculating a derivative of difference value with respect to time; comparing this derivative to a threshold value; and determining that there is tissue damage if the derivative exceeds the threshold value. In an aspect, the method is performed at a plurality of locations.

In an aspect, a difference value of the maximum average pressure value and the minimum average pressure value for each time is indicative of tissue damage. In an aspect, the derivative of difference value with respect to time is calculated from two different times.

In an aspect, the derivative of difference value with respect to time is calculated from the two most recent difference values. In an aspect, the derivative of difference value with respect to time is calculated from the difference value measured at two consecutive timepoints. In an aspect, the derivative of difference value with respect to time is calculated from the difference value measured at two non-consecutive timepoints. In an aspect, a derivative that is positive is indicative of worsening tissue damage. In an aspect, a derivative that is positive is indicative of a pressure ulcer forming.

In one aspect, the present disclosure provides for, and includes, a method of detecting tissue damage before it is visible on a patient's skin, the method comprising the steps of: taking a plurality of pressure measurements at a location on the patient's skin at each of a plurality of incremental times; determining an average pressure value from each of the plurality of pressure measurements; calculating a difference value of the maximum average pressure value and the minimum average pressure value for each incremental time; fitting a curve to a predetermined number of the most-recent difference values; calculating a curvature of the fitted curve; comparing this curvature to a threshold value; and determining that there is tissue damage if the curvature exceeds the threshold value. In an aspect, the method is performed at a plurality of locations.

In an aspect, the curvature of a fitted curve of difference value over time is indicative of tissue damage. In an aspect, an increased curvature of a fitted curve of difference value over time is indicative of worsening tissue damage. In an aspect, an increased curvature of a fitted curve of difference value over time is indicative of a pressure ulcer forming.

In some aspects, a plurality of pressure measurements are taken at incremental times. In an aspect, incremental times is about once every second, about once every 15 seconds, about once every 30 seconds, about once every minute, about once every 10 minutes, about once every 15 minutes, about once every 30 minutes, about once every hour, about once every 2 hours, about once every 3 hours, about once every 4 hours, about once every 6 hours, about once every 12 hours, about once every 24 hours, about once every day, about once every 2 days, about once every 3 days, about once every 4 days, about once every 5 days, about once every 6 days, about once every 7 days, about once every 8 days, about once every 9 days, about once every 10 days.

In an aspect, a threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, a number of pressure values above a predefined threshold value is an indication of sub-epidermal damage that may lead to a pressure ulcer. The time interval between the time when the pressure value first equals or exceeds this threshold and the development of visible symptoms of a pressure ulcer may be a first duration when the pressure value increases linearly. A first duration may be 5 or more days, such as 6 or more days, 7 or more days, 8 or more days, 9 or more days, or 10 or more days.

In another aspect, when the plot of pressure values over time shows an upward curvature or other deviation above a linear progression, the visible symptoms may be present within a shorter amount of time, for example 2-3 days, 1-4 days. 1-3 days, 1-2 days, or 2-4 days. These pressure values are tracked and the trend of the pressure values, i.e. the slope and curvature of a curve connecting these pressure values, are analyzed. In an aspect, the amount by which an incremental pressure value is above a linear prediction based on prior pressure value is compared to a predetermined threshold. In an aspect, the amount by which an incremental pressure value is above the most recent prior pressure value is compared to a predetermined threshold. In an aspect, a curvature of the best-fit curve fitted to a predefined number of the most-recent pressure values is compared to a predetermined threshold. In an aspect, the number of sequential pressure values that exceeds a predetermined value threshold is compared to a number-of-readings threshold. In each of these aspects, the pressure measurement scanner provides a notification when the comparison parameter exceeds the respective threshold.

In an aspect, the trend analysis may ignore a single pressure value that is below a threshold if both the prior and subsequent pressure values are above the threshold.

In an aspect, the trend curve of the pressure values is a point-to-point linear connection. In an aspect, the trend curve is a best-fit curve fitted to the pressure values. In an aspect, the fitted curve is required to intersect the most-recent number of pressure value.

Having now generally described the invention, the same will be more readily understood through reference to the following examples that are provided by way of illustration, and are not intended to be limiting of the present disclosure, unless specified.

EXAMPLES

Example 1: Intervention Levels for Treating Pressure Ulcers in the Heel

Subjects identified as being at risk for pressure ulcers in the heel are treated in accordance with the following scheme:

One or more pressure measurements of the patient at the heel are obtained. The average pressure value is calculated. As shown in Table 1, the patient is assigned an intervention level based on the average pressure value compared to a threshold intensity. Appropriate interventions corresponding to the assigned intervention levels are performed. Subsequent pressure measurements are also performed at a frequency determined by the assigned intervention level. The assigned intervention level of the patient may be changed (increased or decreased) or kept the same depending on the average pressure value of the subsequent measurements.

TABLE 1

EXAMPLE INTERVENTION SCHEME FOR TREATING A PRESSURE ULCER IN THE HEEL

| Intervention Level | Intervention | Frequency of Subsequent Pressure Measurement Monitoring | Corresponding Pressure Value Ranges |
|---|---|---|---|
| 0 | provide good nutrition, standard mattress, and/or turn every 24 hours | every 24 hours | pressure value ≤ threshold |
| 1 | provide a heel boot | every 10 hours | threshold < pressure value ≤ 105% threshold |
| 2 | change of support surface | at the beginning of each nursing shift | 105% threshold < pressure value ≤ 110% threshold |
| 3 | apply dressing to back or sides of heel | every 12 hours | 110% threshold < pressure value ≤ 115% threshold |
| 4 | change to low-friction sheet cover | every 8 hours | 115% threshold < pressure value ≤ 120% threshold |
| 5 | provide a low-friction padded mattress surface for lower leg | every 6 hours | 120% threshold < pressure value ≤ 125% threshold |
| 6 | turn patient at a shorter interval | every 4 hours | 125% threshold < pressure value ≤ 130% threshold |
| 7 | apply barrier cream | every 2 hours | 130% threshold < pressure value ≤ 135% threshold |
| 8 | apply neuro-muscular stimulation | every 1 hour | 135% threshold < pressure value ≤ 145% threshold |
| 9 | apply topical cream to enhance perfusion | every 30 minutes | 145% threshold < pressure value ≤ 150% threshold |
| 10 | provide silicone pad for lower leg | every 15 minutes | 150% threshold < pressure value |

Example 2: Intervention Levels for Treating Pressure Ulcers in the *Sacrum*

Subjects identified as being at risk for pressure ulcers in the *sacrum* are treated in accordance with the following scheme:

One or more pressure measurements of the patient at the *sacrum* are obtained. The average pressure value is calculated. As shown in Table 2, the patient is assigned an intervention level based on the average pressure value compared to a threshold intensity. Appropriate interventions corresponding to the assigned intervention levels are performed at the *sacrum*. Subsequent pressure measurements are also performed at a frequency determined by the assigned intervention level. The assigned intervention level of the patient may be changed (increased or decreased) or kept the same depending on the average pressure value of the subsequent measurements.

TABLE 2

EXAMPLE INTERVENTION SCHEME FOR TREATING A PRESSURE ULCER IN THE SACRUM

| Intervention Level | Intervention | Frequency of Subsequent Pressure Measurement Monitoring | Corresponding Pressure Value Ranges |
|---|---|---|---|
| 0 | provide good nutrition, standard mattress, and/or turn every 24 hours | every 24 hours | pressure value ≤ threshold |
| 1 | reposition patient with wedge and/or keep sacrum dry | every 10 hours | threshold < pressure value ≤ 110% threshold |
| 2 | change mattress to pressure-alleviating mattresses | at the beginning of each nursing shift | 110% threshold < pressure value ≤ 120% threshold |
| 3 | apply dressing over sacrum | every 12 hours | 120% threshold < pressure value ≤ 130% threshold |
| 4 | change to dynamic mattress | every 8 hours | 130% threshold < pressure value ≤ 140% threshold |
| 5 | apply barrier cream | every 6 hours | 140% threshold < pressure value ≤ 150% threshold |
| 6 | apply neuro-muscular stimulation | every 4 hours | 150% threshold < pressure value ≤ 160% threshold |
| 7 | apply topical cream to enhance perfusion | every 2 hours | 160% threshold < pressure value ≤ 170% threshold |
| 8 | provide silicone pad under the patient's body | every 1 hour | 170% threshold < pressure value ≤ 180% threshold |

Example 3: Treatment Decision Pathway for Stratifying Patients and Providing Appropriate Treatments Pressure ulcers are categorized as Stage 1 through Stage 4, with Stage 1 being the least severe. The National Pressure Ulcer Advisory Panel (NPUAP) has defined a Stage 1 ulcer as having intact skin with a localized area of non-blanchable erythema. The erythema (superficial reddening of skin) is "blanchable" if it turns white when pressed and "non-blanchable" if it remains red when pressed, likely due to the presence of red blood cells outside of blood vessels (extravasation). In some patients, blanchable erythema or changes in sensation, temperature, or firmness may precede visible changes. While all patients are potentially at risk, pressure ulcers are more likely to develop in patients who are seriously ill, or those who have a neurological condition, impaired mobility, impaired nutrition, poor posture, or a deformity.

Visual skin assessment (VSA) is the current method of identifying a pressure ulcer. A trained healthcare professional assesses the appearance of the skin, visually and tactilely, looking for redness or variations in tissue firmness, tissue temperature, or moisture.

FIG. 1A outlines the current recommended treatment decision pathway for preventing pressure ulcers in hospital patients, as presented by The National Institute for Health and Care Excellence (NICE) in their clinical guideline *Pressure ulcers: prevention and management*, published 23 April, 2014. The guidelines recommend that a risk analysis be performed for every patient admitted to a care facility that exhibits one or more risk factors, such as significantly limited mobility, a significant loss of sensation, a previous or current pressure ulcer, a nutritional deficiency, an inability to reposition themselves, or a significant cognitive impairment. Risk assessment is commonly done using a scored checklist, such as the Braden Scale, that assesses the severity of specific risk factors. See, e.g., Bergstrom et al., Nurs Res, 36(4): 205-210 (1987). The scale is composed of six subscales that reflect sensory perception, skin moisture, activity, mobility, friction and shear, and nutritional status.

Through the risk assessment, the patient is identified as (i) having a low risk of developing a pressure ulcer, (ii) being at risk of developing a pressure ulcer, or (iii) being at high risk of developing a pressure ulcer. Depending on the level of risk the patient is classified as having, the patient undergoes different sequences of treatment and follow-up evaluation by visual assessment.

If a patient is identified as having a low risk of developing a pressure ulcer, the patient is simply monitored for a change in clinical status, for example, events such as undergoing surgery, worsening of an underlying condition, or a change in mobility. A patient who uses a wheelchair or sits for prolonged periods may be provided with a high-specification foam chair cushion or an equivalent pressure-distributing cushion. If there is no change in clinical status, a low-risk patient will not be reassessed under this set of guidelines and stays within the same treatment and evaluation pathway until he or she is discharged from the care facility.

If a patient is identified as being at risk of developing a pressure ulcer, the patient will be scheduled to be repositioned, or "rounded," every 6 hours. As with the low-risk patient, a high-spec foam chair cushion may be provided if the patient uses a wheelchair or sits for prolonged periods of time. No other monitoring or intervention is recommended under the NICE guidelines.

If a patient is identified as having a high risk of developing a pressure ulcer, the patient will receive a high-spec foam mattress as a preventative measure, or is provided with a high-spec chair cushion if they are in a wheelchair or sit for prolonged periods of time. The patient will also be repositioned every 4 hours. The patient will receive a daily VSA for all areas of the body. If an area is found to have non-blanchable erythema, an appropriate intervention will be implemented and that area re-checked by VSA every 2 hours. Areas that do not exhibit non-blanchable erythema are re-checked daily by VSA. A personalized care plan will be developed for each high-risk patient.

This flow chart (FIG. 1A) shows that caregivers spend the majority of their time on high-risk patients. While this may be appropriate, it leaves the at-risk patients unmonitored, and they may develop a Stage 1 ulcer before the condition is detected by a caregiver. Furthermore, relying on VSA to detect a problem necessarily means that patients will develop a Stage 1 ulcer before an intervention is selected or implemented. By the time that the damage has progressed to Stage 1, it is likely that the skin will break and become a Stage 2 ulcer despite intervention. There is a clear need to identify tissue damage earlier so that interventions can prevent progression of the subepidermal damage to Stage 1 and beyond.

Figure 1B:
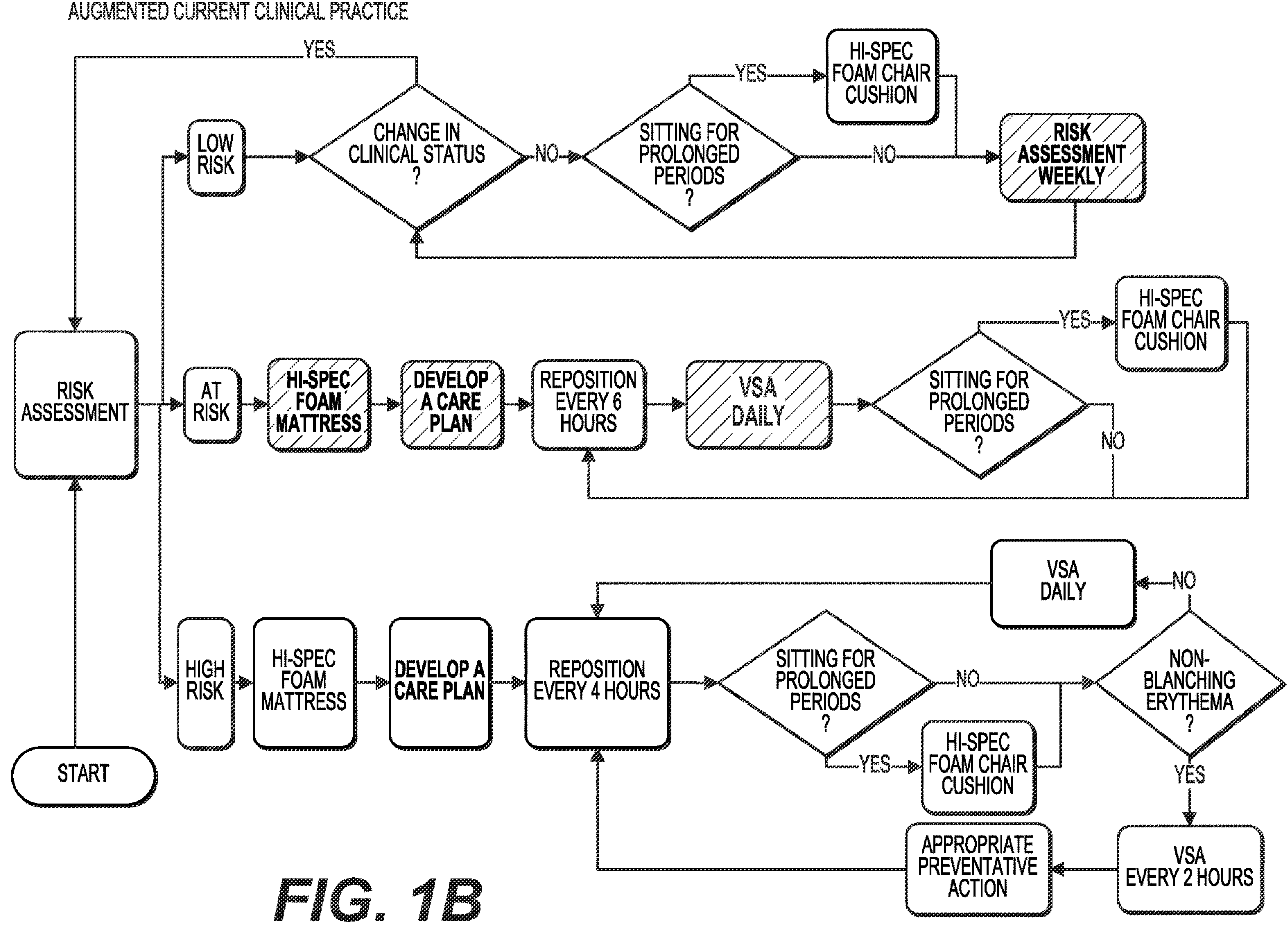
FIG. 1B is an example of a current augmented treatment decision pathway for preventing pressure ulcers as currently implemented at some health care facilities.

FIG. 1B is an example of an augmented treatment decision pathway for preventing pressure ulcers as currently implemented at some health care facilities. The augmented pathway adds monitoring steps to both the at-risk and the low-risk paths. A low-risk patient will receive a weekly risk assessment, for example completion of a Braden Scale assessment. An at-risk patient will receive a high-spec foam mattress as a preventative measure and will be evaluated daily by VSA. A care plan will be developed for monitoring and treating the at-risk patient. No change is made in the care of a high-risk patient.

The augmented plan has the benefit of providing basic monitoring of all patients for pressure ulcers. However, the additional steps will require additional time, either by requiring more staff or further burdening the existing staff. While superior to the recommended care pathway of FIG. 1A, the care pathway of FIG. 1B requires more resources and still suffers from the limitation that a patient must develop a Stage 1 ulcer before VSA identifies the damage.

Different hospitals and care facilities use different numbers of risk categories. They range from two categories (low-risk and at-risk) to four or more categories, with the addition of categories such as "very-high-risk" to those shown in example of FIG. 1B. Patients are assigned to the various categories based on the results of the initial risk assessment.

Figure 2:
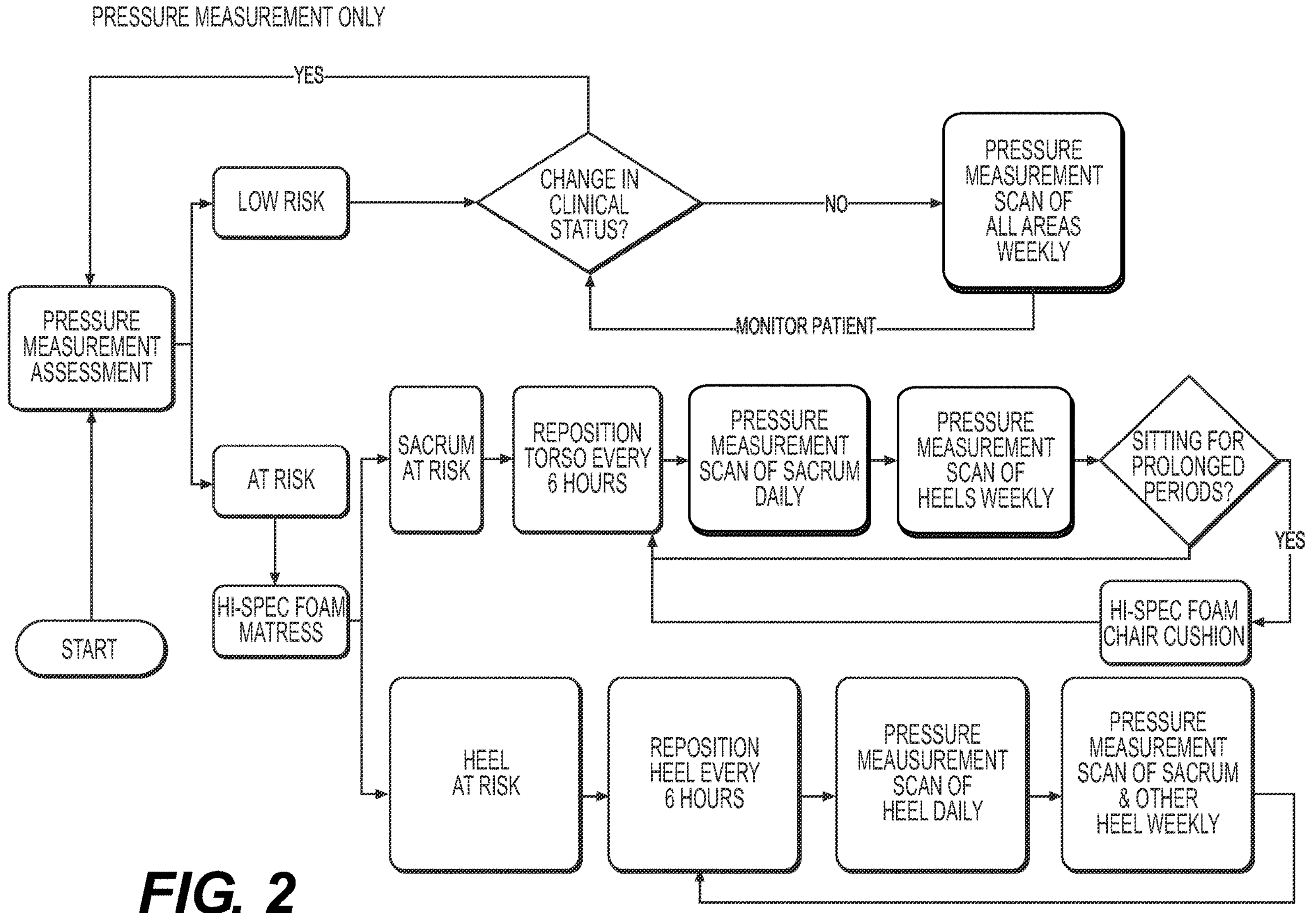
FIG. 2 is an example flowchart of how an apparatus for assessing pressure characteristics on a patient's skin may be used in a stand-alone process to prevent pressure ulcers, in accordance with the present disclosure.

FIG. 2 is an example flowchart of how an apparatus for assessing pressure measurements on a patient's skin may be used in a stand-alone process to prevent pressure ulcers, in accordance with the present disclosure. Every incoming patient receives a complete pressure measurement assessment of all body locations that are selected for monitoring. These selected locations may include areas recommended in the Instructions For Use (IFU) of the pressure measurement apparatus, such as the *sacrum* and the heels. Additional locations may be identified by the hospital and integrated into their in-house practice. Multiple pressure measurements are taken at and around each selected body location, at positions that are spatially distinct from each other. The average pressure value for each location from the set of measurements is calculated at and around that location. The average pressure value is then compared to one or more threshold values to categorize a patient.

In this example, the patient is assigned to one of two risk categories: low-risk and at-risk. A low-risk patient receives weekly pressure measurements of all body locations that are selected for monitoring. This is a small cost that provides benefit for even the healthiest patients, as weekly pressure measurement scans are more likely to detect tissue damage before it becomes visible to VSA.

At-risk patients, who will include patients that would have been identified as high-risk in the current care pathways of FIGS. 1A and 1B, will receive specialized care based on the body location that exhibits a pressure value above a threshold. For example, if the *sacrum* has an pressure value above a threshold, the patient will be repositioned every 6 hours and receive further pressure measurements of the *sacrum* every day, while other body locations like the heel receive weekly pressure measurements.

Figure 3:
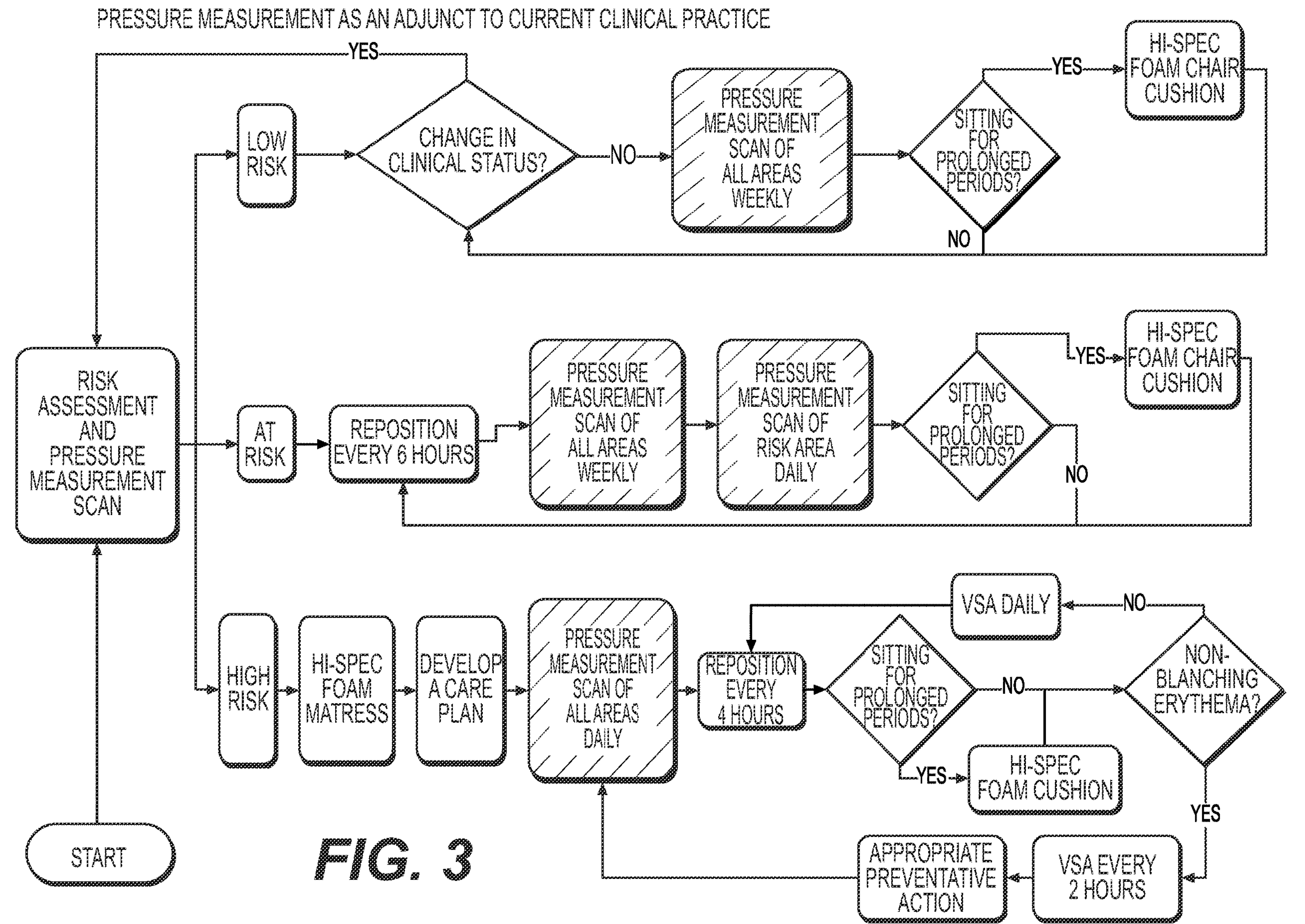
FIG. 3 is an example flowchart of how an apparatus for assessing pressure characteristics on a patient's skin may be used as an adjunct to further improve the augmented treatment decision pathway of FIG. 1B, in accordance with the present disclosure.

FIG. 3 is a flowchart of how an apparatus for measuring pressure on a patient's skin may be used as an adjunct to further improve the augmented treatment decision pathway of FIG. 1B, in accordance with the present disclosure. An incoming patient receives both a risk assessment and a pressure measurement scan of all body locations identified by the hospital for monitoring, and the assignment of a patient to a risk category is based partially on the risk assessment and partially on the pressure measurement scan. An initial pressure value that is greater than a threshold is an indication that there is possible damage at that body location.

A decision whether to implement an intervention, for example turning the patient at a first interval, is currently based on the VSA and risk assessment despite the uncertainty of whether there is early stage damage below the skin.

However, when pressure measurement is used as an adjunct to the augmented treatment decision pathway as shown in FIG. 3, the decision to implement an intervention at a particular body location, is based on the pressure value found for that site in the pressure measurement scan. If the pressure value is less than a predetermined threshold, no intervention is required. If the pressure value is greater than the predetermined threshold, then an intervention is selected and implemented based partially on the body location and partially on the pressure value for that body location. The predetermined threshold for whether or not to select and implement an intervention may be higher or lower than the threshold for determination that there is possible damage at the body location.

A comparison of the costs of providing the care pathways depicted in FIGS. 1A, 1B, 2, and 3 reveals one of the benefits of utilizing a pressure measurement apparatus to monitor patients. Note that the costs cited herein are for patients who do not have or develop pressure ulcers, in which case the estimated treatment cost jumps to $2000 for a Stage 1 ulcer.

The baseline for this comparison is the augmented current practice of FIG. 1B, which represents a current "best practice" for hospitals striving to reduce the incidence rate of pressure ulcers. Providing the care of the low-risk care pathway is expected to cost an average of $26 per patient for the average hospital stay of 5.6 days, while the care for an at-risk patient is estimated to cost an average of $121, and that for a high-risk patient is expected to cost $165. All of the current care pathways rely on a VSA to detect a pressure ulcer and are otherwise implementing interventions based on "typical" patient progression rather than the particular patient's condition.

Integrating an pressure measurement apparatus into the current "best practice" workflow, as shown in FIG. 3, does not lower the cost of any of the care pathways as no work element is being eliminated. However, the benefit lies in the ability to detect tissue damage at an earlier stage at a minimal incremental cost. The incremental cost of adding a pressure measurement scan to the low-risk care pathway is $2, raising the cost from approximately $26 to $28. The expected cost of caring for an at-risk patient who does not have an elevated pressure value, i.e. does not have subepidermal tissue damage, is also increased by only $2. If an at-risk patient is found to have an elevated pressure value, however, the patient is escalated to the high-risk category, where the expected cost of care increases from $165 to $169. This represents a small additional cost for the benefit of earlier detection of tissue damage in low-risk and at-risk patients.

FIG. 2 represents an example workflow that forgoes the routine VSA and relies solely on a pressure measurement apparatus to monitor patients. The expected cost of preventative care for a low-risk patient is $4 using pressure measurement only, compared to the $28 cost using the integrated low-risk care pathway of FIG. 3. For an at-risk patient using pressure measurement only as shown in FIG. 2, the expected cost is $97, compared to the $123-$169 cost for the at-risk and high-risk patients of the integrated care pathway of FIG. 3.

Example 4: Risk Levels Based on Pressure Values

Subjects identified as being at risk for pressure ulcers are treated in accordance with the following scheme:

One or more pressure measurements of the patient at one or more target body locations are obtained. For each body location scanned, the average pressure value is calculated. The average pressure value at different body locations of a number of patients with and without pressure injuries had previously been taken, and used to construct a histogram of the average pressure values. As shown in Table 3, a patient with average pressure values that fall within the first tertile (<33.3% maximum intensity) is assigned to a risk level of zero, while patients with average pressure values that fall within the second tertile (33.3%-66.6% maximum intensity) and third tertile (>66.6% maximum intensity) are assigned to a risk level of one and two respectively. Appropriate interventions corresponding to the assigned risk levels are performed. Subsequent pressure measurements are also performed at a frequency determined by the assigned intervention level. The assigned intervention level of the patient may be changed (increased or decreased) or kept the same depending on the average pressure value of the subsequent measurements.

TABLE 3

EXAMPLE INTERVENTION SCHEME FOR TREATING A PATIENT AT RISK FOR PRESSURE ULCER

| Risk Level | Intervention | Frequency of Subsequent Pressure Measurements | Corresponding Pressure Value Ranges |
|---|---|---|---|
| 0 | provide good nutrition, standard mattress, and/or turn once every 24 hours | every 24 hours | pressure value < 33% of maximum intensity |
| 1 | provide a heel boot; apply dressing to back or sides of anatomic sites at risk for pressure ulcers; change of support surfaces; turn patient at a shorter interval | every 4 hours | 33% of maximum intensity ≤ pressure value < 66% of maximum intensity |
| 2 | provide a low-friction padded mattress surface; keep patient's body dry; turn every 1-2 hours | every 1 hour | 66% of maximum intensity ≤ pressure value ≤ maximum intensity |

From the foregoing, it will be appreciated that the present invention can be embodied in various ways, which include but are not limited to the following:

Embodiment 1. A method of assessing pressure measurements on a patient's intact skin, the method comprising the steps of: (a) obtaining a pressure measurement scan on the patient's skin, and (b) generating a pressure measurement map.

Embodiment 2. A method of reducing the incidence of tissue damage in patients admitted to a care facility, the method comprising the steps of: (a) evaluating a patient for a risk of tissue damage upon admission to the care facility, wherein evaluating comprises: (i) taking a pressure measurement of the patient at one or more body locations at risk of wound development, and (ii) determining an average pressure value of the pressure measurements; (b) administering an intervention of level-0 if the average pressure value is below a first threshold, and (c) administering an intervention of level-N if the average pressure value exceeds the first threshold, wherein N is an integer and N has a value of 1 or greater.

Embodiment 3. The method of embodiment 2, wherein the one or more body locations at risk of wound development are selected from the group consisting of a sternum, a *sacrum*, a heel, a *scapula* (os *latum scapularum*), an elbow, an ear, and other fleshy tissues over a bony prominence of a patient.

Embodiment 4. The method of embodiment 2 or 3, wherein the one or more body locations at risk of wound development comprise one or more anatomical sites in long-term contact with a medical device.

Embodiment 5. The method of embodiment 4, wherein the body location at risk of wound development is selected from the group consisting of a cheek, a nose, a chest, a stomach, and a lower abdomen area.

Embodiment 6. A method of stratifying a plurality of patients in a care facility based on care levels, the method comprising the steps of: (a) taking a pressure measurement of a patient in the plurality of patients at one or more body locations selected for monitoring; (b) determining an average pressure value of the pressure measurement of the patient; (c) determining a care level of N care levels that corresponds to the average pressure value; (d) assigning the care level to the patient; and (e) arranging the patient of the plurality of patients into groups based on each of the patient's assigned care levels.

Embodiment 7. The method of embodiment 6, wherein the one or more body locations at risk of wound development are selected from the group consisting of a sternum, a *sacrum*, a heel, a *scapula* (os *latum scapularum*), an elbow, an ear, and other fleshy tissues over a bony prominence of a patient.

Embodiment 8. The method of embodiment 6 wherein one or more body locations at risk of wound development comprise one or more anatomical sites in long-term contact with a medical device, and are selected from the group consisting of a cheek, a nose, a chest, a stomach, and a lower abdomen area.

Embodiment 9. A method for identifying and providing an appropriate level of care to a patient in a care facility, the method comprising the steps of: (a) taking a plurality of pressure measurements of the patient at one or more body locations; (b) determining an average pressure value of the plurality of pressure measurements of the patient; (c) providing one or more anatomy-specific interventions based on the average pressure value; (d) increasing the level of anatomy-specific interventions based on an increase in the average pressure value; and (e) decreasing the level of anatomy-specific interventions based on a decrease in the average pressure value.

Embodiment 10. A method of assigning a patient in a care facility to a risk category selected from a plurality of risk categories, the method comprising the steps of: (a) taking an initial pressure measurement at one or more locations of the body selected for monitoring; (b) determining an average pressure value of the pressure measurement; and (c) assigning the patient to a risk category selected from the plurality of risk categories, wherein the assigning is based partially on the average pressure value of the pressure measurement.

Embodiment 11. The method of embodiment 10, wherein the locations of the body are selected from the group consisting of a sternum, a *sacrum*, a heel, a *scapula* (os *latum scapularum*), an elbow, an ear, and other fleshy tissues over a bony prominence of a patient.

Embodiment 12. The method of embodiment 10, wherein the locations of the body comprise one or more anatomical sites in long-term contact with a medical device, and are selected from the group consisting of a cheek, a nose, a chest, a stomach, and a lower abdomen area.

Embodiment 13. A method of managing care of a patient, the method comprising the steps of: (a) taking a first set of pressure measurements at one or more body locations selected for monitoring upon admission to a care facility; (b) determining a first average pressure value of each of the first set of pressure measurements; (c) setting an intervention level to N=1 if one of the average pressure value of the first set of pressure measurements is above a first threshold; (d) implementing a level-N intervention for each of the one or more body locations having an average pressure value above a first threshold; (e) taking subsequent sets of pressure measurements at each of the one or more body locations at a level-N frequency; and (f) determining new average pressure values for each of the one or more body locations.

Embodiment 14. The method of embodiment 13, wherein the one or more body locations selected for monitoring are selected from the group consisting of a sternum, a *sacrum*, a heel, a *scapula* (os *latum scapularum*), an elbow, an ear, and other fleshy tissues over a bony prominence of a patient.

Embodiment 15. The method of embodiment 13, wherein one or more body locations selected for monitoring comprise one or more anatomical sites in long-term contact with a medical device, and are selected from the group consisting of a cheek, a nose, a chest, a stomach, and a lower abdomen area.

Embodiment 16. A method of identifying and treating a patient at risk of tissue damage, the method comprising the steps of: (a) evaluating a patient for a risk of tissue damage upon admission to a care facility, wherein the evaluating step comprises: (i) taking a first plurality of pressure measurements in the patient; and (ii) determining a first average pressure value of the initial set of pressure measurements; (b) administering a first intervention of level-0 if the first average pressure value is below or equal to a first threshold; and (c) administering a first intervention of level-N if the first average pressure value is above the first threshold, where N is an integer and N has a value of 1 or greater.

Embodiment 17. The method of embodiment 16, further comprising the steps of: (a) taking a second plurality of pressure measurements in the patient at a first pre-determined frequency corresponding to the administered intervention level; (b) determining a second average pressure value of the second plurality of pressure measurements; (c) determining whether the second average pressure value exceeds a second threshold; (d) continuing to administer the first intervention if the second average pressure value does not exceed the second threshold; (e) continuing to take a plurality of pressure measurements at the first pre-determined frequency if the second average pressure value does not exceed the second threshold; (f) administering a second intervention of level-M if the second average pressure value exceeds the second threshold, where M is an integer and M is greater than N; and (g) taking a plurality of pressure measurements at a second pre-determined frequency corresponding to level-M if the second average pressure value exceeds the second threshold.

Embodiment 18. The method of embodiment 16 or 17, further comprising the steps of: (a) determining whether the second average pressure value is less than a third threshold; (b) continuing to administer the first intervention if the second average pressure value is not less than the third threshold; (c) continuing to take a plurality of pressure measurements at the first pre-determined frequency if the second average pressure value is not less than the third threshold; (d) administering a third intervention of level-L if the second average pressure value is less than the third threshold and if the first intervention is not of level-0, where L is an integer and L is less than N; and (e) taking a plurality of pressure measurements at a pre-determined frequency corresponding to level-L if the second average pressure value is less than the third threshold.

Embodiment 19. The method of any one of embodiments 16-18, wherein the first intervention of level-N is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 20. The method of any one of embodiments 17-19, wherein the second intervention of level-M is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 21. The method of any one of embodiments 18-20, wherein the third intervention of level-L is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 22. The method of any one of embodiments 16-21, wherein the first average pressure value is determined from a subset of the first plurality of pressure measurements.

Embodiment 23. The method of any one of embodiments 17-22, wherein the second average pressure value is determined from a subset of the second plurality of pressure measurements.

Embodiment 24. The method of any one of embodiments 17-23, wherein the second threshold is equal to the first threshold.

Embodiment 25. The method of any one of embodiments 18-24, wherein the third threshold is equal to the first threshold.

Embodiment 26. A method of identifying and treating a patient in need of an intervention for pressure ulcer, the method comprising the steps of: (a) taking a plurality of pressure measurements at an anatomic site of the patient; (b) determining an average pressure value of the plurality of pressure measurements; (c) determining whether the average pressure value exceeds a threshold corresponding to level N, where N is greater than or equal to 2; (d) administering the intervention for pressure ulcer to the anatomic site if the average pressure value exceeds the threshold; and (e) taking a plurality of pressure measurements every two hours if the average pressure value exceeds the threshold.

Embodiment 27. The method of embodiment 26, wherein the anatomical site is selected from the group consisting of a sternum, a *sacrum*, a heel, a *scapula* (os *latum scapularum*), an elbow, an ear, and other fleshy tissues over a bony prominence of a patient.

Embodiment 28. The method of embodiment 26 or 27, wherein the intervention for pressure ulcer is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 29. A method for identifying damaged tissue, the method comprising the steps of: (a) obtaining a first pressure measurement from a first location on a patient's skin; (b) obtaining a second pressure measurement from a second location that is bisymmetric relative to the first location; (c) determining an average pressure value of each of the first and second pressure measurements; (d) determining a difference in the average pressure value between a first pressure measurement and a second pressure measurement; and (e) determining that there is tissue damage at the first or second location if the difference in average pressure value exceeds a threshold value.

Embodiment 30. The method of embodiment 29, wherein the first location is selected from the group consisting of a sternum, a *sacrum*, a heel, a *scapula* (os *latum scapularum*), an elbow, an ear, and other fleshy tissues over a bony prominence of a patient.

Embodiment 31. A method of detecting tissue damage before it is visible on a patient's skin, the method comprising the steps of: (a) taking a plurality of pressure measurements at a location on the patient's skin at incremental times; (b) determining an average pressure value from each of the plurality of pressure measurements; (c) calculating a slope between the latest average pressure value and the immediately prior average pressure value; (d) comparing the slope to a threshold value; and (e) determining that there is tissue damage if the slope exceeds the threshold value.

Embodiment 32. The method of embodiment 31, wherein the location is selected from the group consisting of a sternum, a *sacrum*, a heel, a *scapula* (os *latum scapularum*), an elbow, an ear, and other fleshy tissues over a bony prominence of a patient.

Embodiment 33. The method of embodiment 31 or 32, wherein the method is performed at a plurality of locations.

Embodiment 34. A method of detecting tissue damage before it is visible on a patient's skin, the method comprising the steps of: (a) taking a plurality of pressure measurements on the patient's skin at a location at incremental times; (b) determining an average pressure value from the each of the plurality of pressure measurements; (c) calculating a pressure difference of the maximum average pressure value and the minimum average pressure value for each time; (d) calculating a derivative of the pressure difference with respect to time; (e) comparing the derivative to a threshold value; and (f) determining that there is tissue damage if the derivative exceeds the threshold value.

Embodiment 35. The method of embodiment 34, wherein the plurality of locations is selected from the group consisting of a sternum, a *sacrum*, a heel, a *scapula* (os *latum scapularum*), an elbow, an ear, and other fleshy tissues over a bony prominence of a patient.

Embodiment 36. The method of embodiment 34 or 35, wherein the derivative of difference value with respect to time is calculated from the two most recent difference values.

Embodiment 37. The method of any one of embodiments 34-36, wherein the method is performed at a plurality of locations.

Embodiment 38. A method of detecting tissue damage before it is visible on a patient's skin, the method comprising the steps of: (a) taking a plurality of pressure measurements at a location on the patient's skin at each of a plurality of incremental times; (b) determining an average pressure value from each of the plurality of pressure measurements; (c) calculating a pressure difference of the maximum average pressure value and the minimum average pressure value for each incremental time; (d) fitting a curve to a predetermined number of the most-recent pressure differences; (e) calculating a curvature of the fitted curve; (f) comparing this curvature to a threshold value; and (g) determining that there is tissue damage if the curvature exceeds the threshold value.

Embodiment 39. The method of embodiments 38 wherein the location is selected from the group consisting of a sternum, a *sacrum*, a heel, a *scapula* (os *latum scapularum*), an elbow, an ear, and other fleshy tissues over a bony prominence of a patient.

Embodiment 40. The method of embodiment 38 or 39, wherein the method is performed at a plurality of locations.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

I claim:

1. A method for identifying and providing an appropriate level of care to a patient in a care facility, the method comprising the steps of:

a) taking a plurality of pressure measurements of the patient at one or more body locations;

b) determining an average pressure value of the plurality of pressure measurements of the patient;

c) providing one or more anatomy-specific interventions based on the average pressure value;

d) increasing the level of anatomy-specific interventions based on an increase in the average pressure value; and e) decreasing the level of anatomy-specific interventions based on a decrease in the average pressure value.

2. A method of managing care of a patient, the method comprising the steps of:

a) taking a first set of pressure measurements at one or more body locations selected for monitoring upon admission to a care facility;

b) determining a first average pressure value of each of the first set of pressure measurements;

c) setting an intervention level to N=1 if one of the average pressure value of the first set of pressure measurements is above a first threshold;

d) implementing a level-N intervention for each of the one or more body locations having an average pressure value above a first threshold;

e) taking subsequent sets of pressure measurements at each of the one or more body locations at a level-N frequency; and f) determining new average pressure values for each of the one or more body locations.

3. The method of claim 2, wherein the one or more body locations selected for monitoring are selected from the group consisting of a sternum, a sacrum, a heel, a scapula (os *latum* scapularum), an elbow, an ear, and other fleshy tissues over a bony prominence of a patient.

4. The method of claim 2, wherein one or more body locations selected for monitoring comprise one or more anatomical sites in long-term contact with a medical device, and are selected from the group consisting of a cheek, a nose, a chest, a stomach, and a lower abdomen area.

5. A method of identifying and treating a patient at risk of tissue damage, the method comprising the steps of:

a) evaluating a patient for a risk of tissue damage upon admission to a care facility, wherein the evaluating step comprises:

i) taking a first plurality of pressure measurements in the patient;

ii) determining a first average pressure value of the first plurality of pressure measurements;

b) administering a first intervention of level-0 if the first average pressure value is below or equal to a first threshold; and c) administering a first intervention of level-N if the first average pressure value is above the first threshold, where N is an integer and N has a value of 1 or greater.

6. The method of claim 5, further comprising the steps of:

a) taking a second plurality of pressure measurements in the patient at a first pre-determined frequency corresponding to the administered intervention level;

b) determining a second average pressure value of the second plurality of pressure measurements;

c) determining whether the second average pressure value exceeds a second threshold;

d) continuing to administer the first intervention if the second average pressure value does not exceed the second threshold;

e) continuing to take a plurality of pressure measurements at the first pre-determined frequency if the second average pressure value does not exceed the second threshold;

f) administering a second intervention of level-M if the second average pressure value exceeds the second threshold, where M is an integer and M is greater than N; and g) taking a plurality of pressure measurements at a second pre-determined frequency corresponding to level-M if the second average pressure value exceeds the second threshold.

7. The method of claim 6, wherein the second intervention of level-M is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

8. The method of claim 6, wherein the second average pressure value is determined from a subset of the second plurality of pressure measurements.

9. The method of claim 6, wherein the second threshold is equal to the first threshold.

10. The method of claim 6, further comprising the steps of:

a) determining whether the second average pressure value is less than a third threshold;

b) continuing to administer the first intervention if the second average pressure value is not less than the third threshold;

c) continuing to take a plurality of pressure measurements at the first pre-determined frequency if the second average pressure value is not less than the third threshold;

d) administering a third intervention of level-L if the second average pressure value is less than the third threshold and if the first intervention is not of level-0, where L is an integer and L is less than N; and e) taking a plurality of pressure measurements at a pre-determined frequency corresponding to level-L if the second average pressure value is less than the third threshold.

11. The method of claim 10, wherein the third intervention of level-L is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

12. The method of claim 10, wherein the third threshold is equal to the first threshold.

13. The method of claim 5, wherein the first intervention of level-Nis selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

14. The method of claim 5, wherein the first average pressure value is determined from a subset of the first plurality of pressure measurements.

15. A method of identifying and treating a patient in need of an intervention for pressure ulcer, the method comprising the steps of:

a) taking a plurality of pressure measurements at an anatomic site of the patient;

b) determining an average pressure value of the plurality of pressure measurements;

c) determining whether the average pressure value exceeds a threshold corresponding to level N, where N is greater than or equal to 2;

d) administering the intervention for pressure ulcer to the anatomic site if the average pressure value exceeds the threshold; and e) taking a plurality of pressure measurements every two hours if the average pressure value exceeds the threshold.

16. The method of claim 15, wherein the anatomical site is selected from the group consisting of a sternum, a sacrum, a heel, a scapula (os *latum* scapularum), an elbow, an ear, and other fleshy tissues over a bony prominence of a patient.

17. The method of claim 15, wherein the intervention for pressure ulcer is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

* * * * *